US011869675B2

(12) United States Patent
Frey et al.

(10) Patent No.: US 11,869,675 B2
(45) Date of Patent: Jan. 9, 2024

(54) PROVIDER DETERMINATION SYSTEM, METHODS FOR DETERMINING PROVIDERS WITHIN A PROVIDER NETWORK, AND METHODS FOR PROVIDING INFORMATION RELATED TO PROVIDERS TO A USER

(71) Applicant: Embold Health, Inc., Nashville, TN (US)

(72) Inventors: Tony Carl Frey, Austin, TX (US); Adam Kneisler, Austin, TX (US)

(73) Assignee: Embold Health, Inc., Austin, TX (US)

( * ) Notice: Subject to any disclaimer, the term of this patent is extended or adjusted under 35 U.S.C. 154(b) by 876 days.

(21) Appl. No.: 16/433,993

(22) Filed: Jun. 6, 2019

(65) Prior Publication Data

US 2020/0388402 A1 Dec. 10, 2020

(51) Int. Cl.
*G16H 80/00* (2018.01)
*G06F 16/9537* (2019.01)
*G06F 40/30* (2020.01)
*H04L 51/10* (2022.01)
*H04L 51/18* (2022.01)

(52) U.S. Cl.
CPC ......... *G16H 80/00* (2018.01); *G06F 16/9537* (2019.01); *G06F 40/30* (2020.01); *H04L 51/10* (2013.01); *H04L 51/18* (2013.01)

(58) Field of Classification Search
CPC ...... G06F 40/30; G06F 16/9537; G06F 16/36; G06F 16/3329; H04L 51/222; H04L 51/10; H04L 51/18; G16H 80/00
See application file for complete search history.

(56) References Cited

U.S. PATENT DOCUMENTS

| | | | | |
|---|---|---|---|---|
| 2010/0145723 A1* | 6/2010 | Hudson | ................... | G06Q 40/00 |
| | | | | 342/357.31 |
| 2014/0288951 A1* | 9/2014 | Zielinski | ................ | G16H 15/00 |
| | | | | 705/2 |
| 2018/0336972 A1* | 11/2018 | Carbonell | ............... | G06F 16/93 |
| 2020/0244605 A1* | 7/2020 | Nagaraja | ................ | G16H 40/67 |

* cited by examiner

*Primary Examiner* — Soe Hlaing
(74) *Attorney, Agent, or Firm* — TraskBritt

(57) ABSTRACT

Methods of providing provider information to a client device includes receiving, from a client device, a request for information for a provider within a user's provider network, generating and providing a request for location information; receiving a location response, determining whether a location identified by the location response is currently supported by the provider determination system, generating and providing a provider type request, receiving a provider type response; determining whether there are providers within the user's provider network that match both the location identified in the location response and a provider type identified in the provide type response, generating and providing a provider list, receiving a provider selection response selecting a provider from the provider list, generating and providing a provider information including information related to the selected provider.

14 Claims, 16 Drawing Sheets

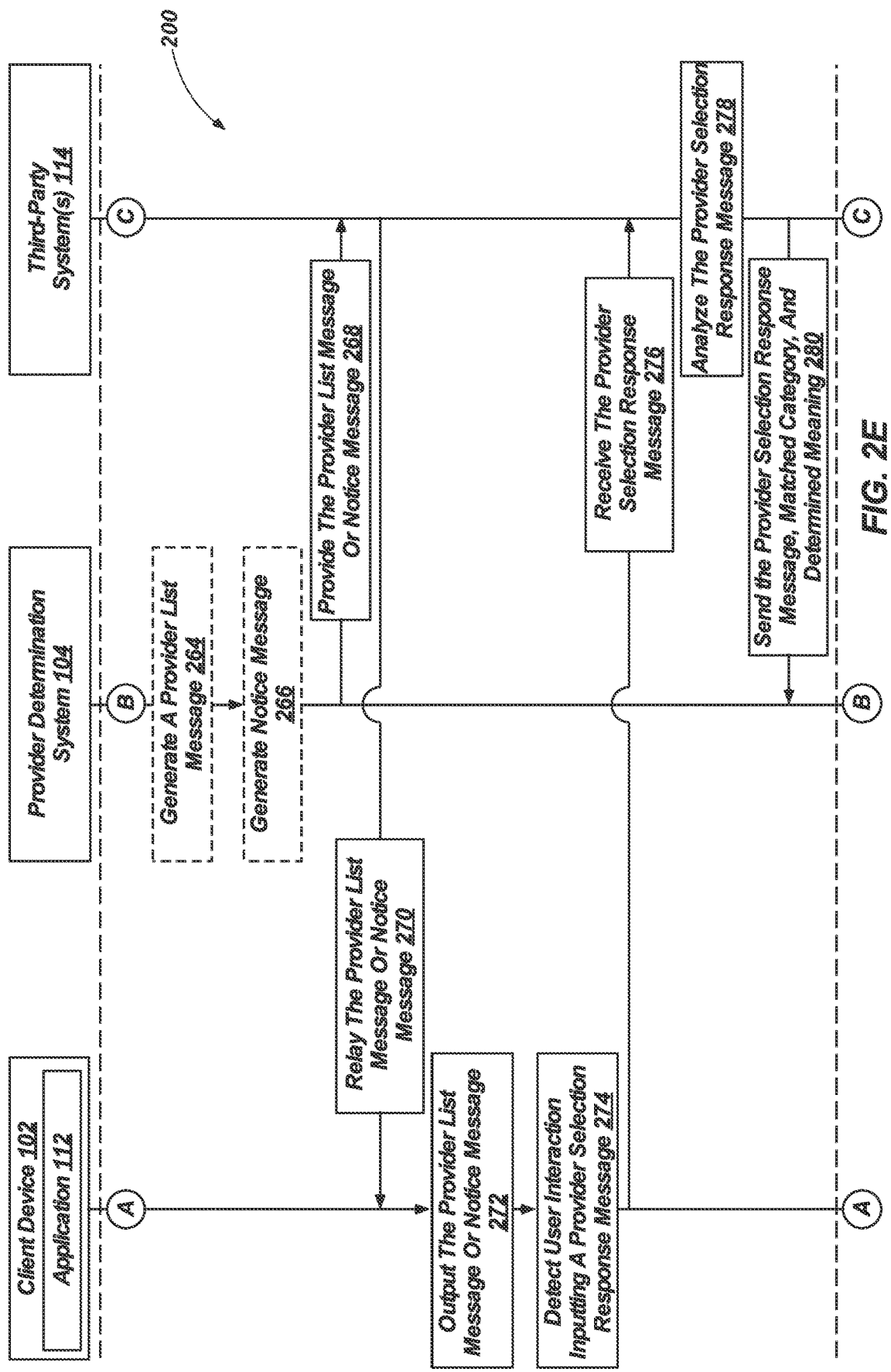

PROVIDER DETERMINATION SYSTEM, METHODS FOR DETERMINING PROVIDERS WITHIN A PROVIDER NETWORK, AND METHODS FOR PROVIDING INFORMATION RELATED TO PROVIDERS TO A USER

TECHNICAL FIELD

This disclosure relates generally to a provider determination system for communicating with a user via a client device and via messages (e.g., SMS messages), determining providers within the user's provider network, and efficiently providing information related to the providers to the user via the client device.

BACKGROUND

Determining whether a given doctor is covered within an insurance plan has typically been a relatively painful process. For instance, conventionally, a user must either, call the insurance network and remain on hold for countless hours before finally speaking with a representative to receive the desired information, or the user must access a website of the insurance network and the search for the provider or search provider list for a provider specialty. Often, the websites are confusing as the lists are generic and do not apply to each insurance network individually. Moreover, the specialties may not be listed in common terms, and the interfaces (e.g., websites) are foreign and difficult to navigate. Additionally, the interfaces often require a substantial amount of information to access any information. For instance, the interfaces generally require a user to input information from an insurance card (e.g., plan and group information) and for the user to create an account just to start a process of searching for a provider. The foregoing often hinders, delays, and/or prevents a user from being able to search for providers. Furthermore, accessing a website to search the insurance network requires a laptop and/or a smartphone with a data plan. The foregoing limitations limit access for some individuals. As a result, users can unintentionally schedule appointments with providers outside of their provider network.

BRIEF SUMMARY

The various embodiments described below provide benefits and/or solve one or more of the foregoing or other problems in the art with systems and methods for determining providers within a provider network. Some embodiments of the present disclosure include a method of accessing a provider directory using messages, natural language processing, and a provider determination system. The method may include receiving, from a client device, a message requesting information for a provider within a user's provider network; analyzing the message via natural language processing to determine a meaning of the message; based on the determined meaning, matching the message with a communication category of the provider determination system; identifying queries based on query parameters identified in the determined meaning of the message and the matched communication category; submitting the queries to a provider database to identify one or more providers that match the identified query parameters; and providing information related to the one or more providers to the client device.

Some embodiments of the present disclosure include a system for providing provider information. The system may include at least one processor and at least one non-transitory computer-readable storage medium storing instructions thereon that, when executed by the at least one processor, cause the system to: receive, from a first client device, a referral request message, in response to receiving the referral request message, generate a request for contact information associated with a second client device, send the request for contact information to the first client device, receive, from the first client device, a contact information response message, in response to receiving the contact information response message, generate a request for a relay message, send the request for a relay message to the second client device, receive, from the first client device, a relay message, send the relay message to the second client device with an invitation to initiate communication with the system via an inquiry message, receive, from the second client device, an inquiry message requesting information for a provider within a user's provider network, in response to receiving a location response message and a provider type response message from the second client device, determine whether there are providers within the user's provider network that match both a location identified in the location response message and a provider type identified in the provide type response message, in response to identifying one or more providers that match both the location identified in the location response message and the provider type identified in the provide type response message, generate a provider list message, send the provider list message to the second client device, receive, from the second client device, a provider selection response message selecting a provider from the provider list message, in response to receiving the provider selection response message, generate a provider information message including information related to the selected provider and send the provider information message to the second client device.

One or more embodiments of the present disclosure include a non-transitory computer-readable medium storing instructions thereon that, when executed by at least one processor, cause the at least one processor to perform steps comprising: receiving, from a client device, an inquiry message requesting information for a provider within a user's provider network, in response to receiving the inquiry message, providing a request for location information and a provider type request to the client device, in response to receiving a location response message and a provider type response message, determining whether there are providers within the user's provider network that match both a location identified in the location response message and a provider type identified in the provide type response message, in response to identifying one or more providers that match both the location identified in the location response message and the provider type identified in the provide type response message, generating a provider list message and providing the provider list message to the client device, in response to receiving a provider selection message selecting a provider from the provider list message, generating a provider information message including information related to the selected provider and an option to initiate an action in related to the selected provider, providing the provider information message to the client device, receiving an indication from the client device to initiate the action related to the selected provider, and initiating the action related to the selected provider.

BRIEF DESCRIPTION OF THE DRAWINGS

Various embodiments will be described and explained with additional specificity and detail through the use of the accompanying drawings in which:

FIGS. 2A-2F illustrate a sequence flow diagram that a provider determination system can utilize to identify providers within a provider network and communicate with a client device in accordance with one or more embodiments;

DETAILED DESCRIPTION

Figure 1:
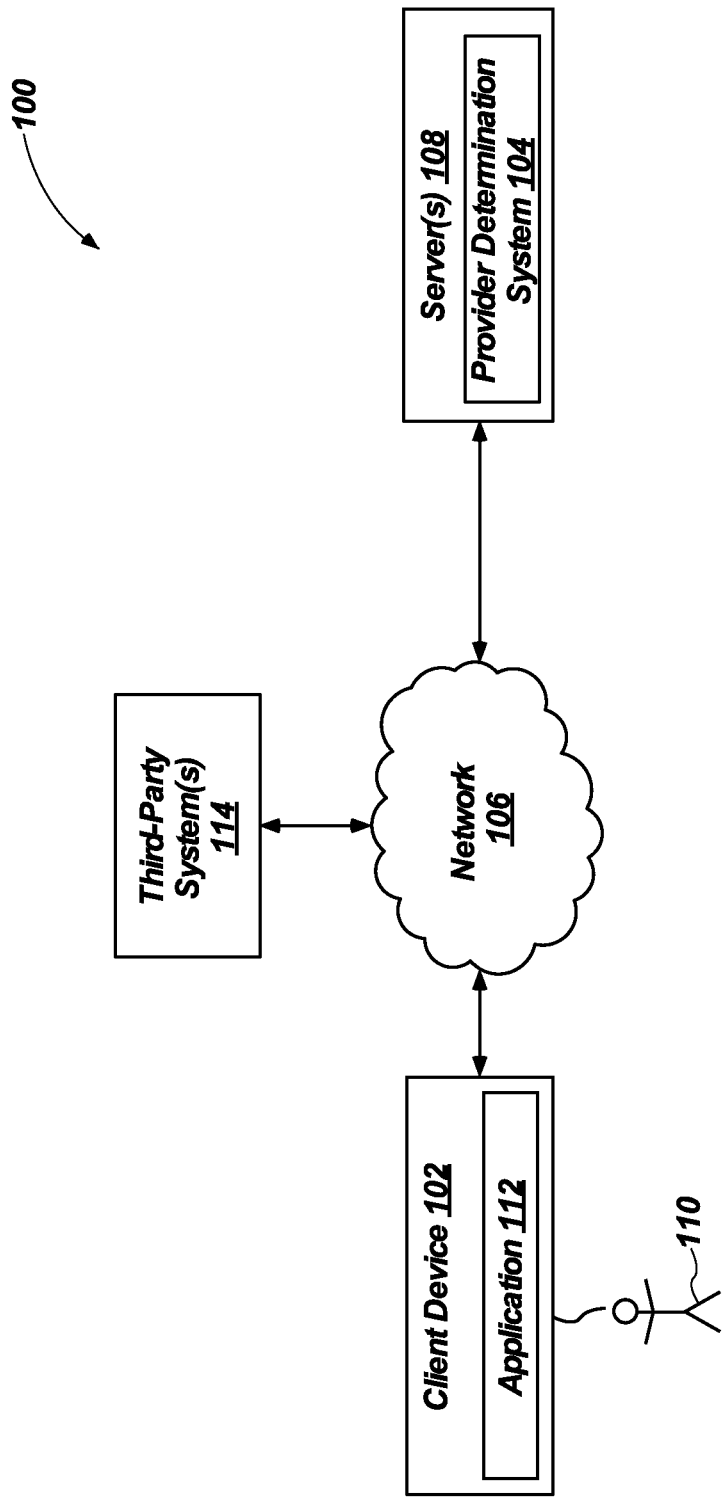
FIG. 1 illustrates a schematic representation of an environment within which a provider determination system can operate in accordance with one or more embodiments of the present disclosure.

The illustrations presented herein are not actual views of any particular provider determination system, or any component thereof, but are merely idealized representations, which are employed to describe the present invention.

As used herein, the singular forms following "a," "an," and "the" are intended to include the plural forms as well, unless the context clearly indicates otherwise.

As used herein, the term "may" with respect to a material, structure, feature, function, or method act indicates that such is contemplated for use in implementation of an embodiment of the disclosure, and such term is used in preference to the more restrictive term "is" so as to avoid any implication that other compatible materials, structures, features, functions, and methods usable in combination therewith should or must be excluded.

As used herein, any relational term, such as "first," "second," etc., is used for clarity and convenience in understanding the disclosure and accompanying drawings, and does not connote or depend on any specific preference or order, except where the context clearly indicates otherwise.

As used herein, the term "substantially" in reference to a given parameter, property, act, or condition means and includes to a degree that one skilled in the art would understand that the given parameter, property, or condition is met with a small degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measurement of the given parameter, as well as variations resulting from manufacturing tolerances, etc.).

As used herein, the term "low-data message" refers to an electronic message (e.g., a text message) that requires a relatively low amount of data (e.g., less than about 150 bytes) to send and/or receive. For example, in some embodiments, a low-data message refers to a short message service (SMS) message. In other embodiments, a low-data message can be a multimedia messaging service (MMS) message, an extensible messaging and presence protocol (XMPP) message, a session initiation protocol (SIP) message, an Internet relay chat (IRC) message, an enhanced message service (EMS) message, an iMessage message, etc. In additional embodiments, the low-data message may include messages sent via WHATSAPP and/or SIGNAL. In some embodiments, a low-data message's content consists primarily or entirely of alpha-numeric characters.

One or more embodiments of the present disclosure include a provider determination system that enables a user via a client device (e.g., a smart phone) and utilizing the provider determination system to quickly and relatively easily find providers (e.g., doctors) within the user's provider network and/or within a given geographic location. For example, the provider determination system provides the ability (e.g., service) for a user to search a provider directory by interfacing with the provider determination system and specifically, a Chatbot architecture, via messages (e.g., a text message communication session). In some embodiments, the provider determination system (e.g., the Chatbot architecture) may receive an initial text message (e.g., an SMS message) from the user, and the provider determination system opens a question/answer session with the user in response to receiving the text message. After requesting location information and a particular provider specialty, the provider determination system may provide an SMS message with information regarding providers near the user's area. In one or more embodiments, the message may include any other type of text message, email, audio message, and/or video message.

In some embodiments, the provider determination system may identify the user's provider network based on the user telephone number or a unique identifying provided by the user. In other embodiments, the provider determination system may identify the user's provider network based on the number (e.g., the telephone number) to which the message from the user was sent. For instance, the provider determination system may identify each provider network supported by the provider determination system.

Because the provider determination system of the present disclosure enables a user to quickly and efficiently receive information related to providers near the user's location via SMS message, the provider determination system is advantageous over provider determination systems. For instance, because the provider determination system uses SMS messages (e.g., low-data messages) for communication, and because the user's device utilizes a relatively small amount of data in comparison to utilizing a desktop and/or laptop computer and provider network website, the provider determination system reduces required processing power, memory, and communication resources needed to facilitate users receiving/accessing information about providers within their provider network. Accordingly, the provider determination system results in less data transfer and data bandwidth usage for a computer/communication system. In other words, the provider determination system results in less required processing power and communication bandwidth in comparison to conventional systems. As a result, the provider determination system of the present disclosure, in comparison to conventional systems, may be a more appropriate system for mobile devices. Additionally, the in view of the foregoing, the provider determination system may result in more user friendly, consistent, attractive, and efficient method for discovering a provider within a provider network in comparison to conventional provider determination systems and methods.

Furthermore, because the provider determination system can communicate with the client device via mere text message (e.g., low-data messages), the provider determination system may provide greater access (e.g., access to the public) for finding providers within a given provider network. In particular, unlike conventional provider determination systems, which often require a desktop and/or laptop to access a provider network website or require a significant usage of cellular data and a relatively strong cellular signal to search databases of providers, the provider determination system only requires sufficient cellular data and/or Wi-Fi signals to send and receive SMS messages (e.g., low-data messages) and may be performed with any phone capable of sending and receiving text message. In other words, the provider determination system does not require a smart phone. In view of the foregoing, the provider determination system of the present disclosure provides a simple, efficient, and relatively quick method to identify a provider within a user's provider network, and the method is accessible to anyone with a phone capable of sending and receiving text messages. Thus, the provider determination system may be utilized in areas without high speed data (i.e., cellular data) signals. Furthermore, the provider determination system may be utilized with tablets (e.g., iPads) and/or desktop computers as well as any other device operating SaaS applications.

Moreover, because the provider determination system can operate by sending and receiving text messages, the provider determination system is accessible to more users, and more users will have access to a phone in comparison to a desktop and/or laptop. Furthermore, the provider determination system removes steps typically necessary for determining whether a provider is within a given provider network (e.g., insurance network). For instance, the provider determination system automatically detects the user's provider network, and automatically searches for providers only within that provider network. As a result, the provider determination system does not require a substantial amount of information from a user (i.e., the provider determination system information) unlike conventional systems. Thus, the provider determination system provides quicker access to provider information for users in comparison to conventional system. Likewise, the provider determination system operates within a familiar interface (e.g., a texting interface) that is widely recognized and easy to navigate.

Additionally, the provider determination system described herein improves a process of searching a directory of providers. In particular, the provider determination system provides natural language processing at a communication interface so that users can send texts to initiate searching of the directory of providers. Additionally, the provider determination system provides automated searching that utilizes queries generated based on the natural language processing and other parameters and then sends (e.g., provides) the results via a text (or any other type of message). Furthermore, the provider determination system increases a speed at which the search results can be provided to a user, increases search results content, and enables more functionality as is described in greater detail herein.

FIG. 1 illustrates a schematic diagram of an environment 100 in which a provider determination system may operate according to one or more embodiments of the present disclosure. As illustrated, the environment 100 includes a client device 102, at least one server 108 including a provider determination system 104, a network 106, and one or more third-party system(s) 114. As used herein, the term "provider determination system" refers to a system that determines (e.g., identifies) providers (e.g., doctors) for a user within a particular provider network (e.g., the user's insurance network) based on received information such as, for example, a location of the user, specialty of a desired provider, a location of the desired provider, an urgency of the user, etc. As used herein, the term "provider" refers generally to a health care provider including any conventional health care provider (e.g., general practitioners (e.g., internal medicine, family practice, emergency room, general surgery doctors, etc.)) and/or specialty doctors (e.g., cardiologists, pediatric doctors, obstetricians and gynecologists, optometrists, ophthalmologists, orthopedic surgeons, etc.). In some embodiments, as is described in greater detail below, the provider determination system 104 may provide a provider-finding service. For instance, the provider determination system 104 may determine (e.g., identify) a provider that is covered (e.g., falls within) the user's provider network (e.g., insurance network, employer network, etc.) and/or provide information to the client device 102 regarding an identified provider. As is described in greater detail below in regard to FIG. 3, in one or more embodiments, the provider determination system 104 may include a dialogue system that forms a Chatbot architecture for engaging in a question/answer session with a user 110 of the client device 102 as part of the provider-finding service described herein.

In some embodiments, the client device 102 may include an application 112 for facilitating communication (e.g., reading, composing, recording, and/or sending messages (e.g., SMS messages)) between the user 110 and third parties and/or the provider determination system 104. In particular, the client device 102 may execute one or more applications (e.g., application 112) for performing the functions of the various embodiments and processes described herein. For example, in some instances, the application 112 may be an electronic messaging application (e.g., a messenger, a chat application, a text messenger, etc.). In some embodiments, the application 112 may include a messenger application or a messenger within a social media application. In additional embodiments, the application 112 may include a skill and/or application of a smart speaker or within a cloud computing service. In further embodiments, the application 112 may be a web browser or email provider application. In yet further embodiments, the application 112 may be a video chat application. In some embodiments, the application 112 may be local to the client device 102. In other embodiments, the application 112 may be stored and/or at least partially operated via a cloud computing service. In one or more embodiments, as is discussed in greater detail in regard to FIGS. 2A-2F, the application 112 of the client device 102 enables communication with (e.g., sending messages (e.g., text, audio, and/or video messages) to and receiving messages from) the provider determination system 104 via the network 106 and/or the third-party systems 114.

In one or more embodiments, the application 112 may be a native application installed on the client device 102. For example, the application 112 may be a mobile application that installs and runs on a mobile device, such as a smart phone or a tablet. In some embodiments, the application 112 facilitates the creation of messages, such as SMS messages, to send to other client devices and/or the provider determination system 104. The application 112 may be a text messaging application that is native to the client device 102 and/or specific to an operating system of the client device 102. Further, the application 112 may be independent of the provider determination system 104 (i.e., the application 112 may be a generic messaging application not tied to the provider determination system 104 and that does not use the provider determination system 104 to send messages). Alternatively, the application 112 may be a client application that is associated with the provider determination system 104 and configured to send messages directly to the provider determination system 104 through the application 112.

The provider determination system 104, the client device 102, and the third-party system(s) 114 may communicate via the network 106. In one or more embodiments, the network 106 includes a combination of cellular or mobile telecommunications networks, a public switched telephone network (PSTN), and/or the Internet or World Wide Web and facilitates the transmission of messages between the client device 102 and the provider determination system 104. The network 106, however, may include various other types of networks that use various communication technologies and protocols, such as a wireless local network (WLAN), a wide area network (WAN), a metropolitan area network (MAN), other telecommunication networks, or a combination of two or more of the foregoing networks. Although FIG. 1 illustrates a particular arrangement of the client device 102, the server 108, the third-party system(s) 114, and the network 106, various additional arrangements are possible. For example, the server 108 and, accordingly, the provider determination system 104, may directly communicate with the client device 102, bypassing the network 106.

As illustrated in FIG. 1, a user 110 may interface with the client device 102, for example, to communicate with the server 108 and to utilize the provider determination system 104 in order to identify providers within the user's provider network by sending and receiving messages within the application 112. The user 110 may be an individual (i.e., human user), a business, a group, or any other entity. Although FIG. 1 illustrates only one user 110 associated with the client device 102, the environment 100 may include any number of a plurality of users that each interact with the environment 100 using a corresponding client device, as is discussed in greater detail below in regard to FIG. 5.

The client device 102 may be any one or more of various types of computing devices. For example, the client device 102 may include a mobile device such as a mobile telephone, a smartphone, a PDA, a tablet, or a laptop, a smart speaker (e.g., AMAZON ECHO™, GOOGLE HOME™, APPLE HOMEPOD®, etc.) or a non-mobile device such as a desktop or another type of computing device. Additional details with respect to the client device 102 are discussed below with respect to FIG. 8.

In some embodiments, a provider determination system 104 may include one or more systems, servers, and/or other devices for identifying providers of within a user's provider network (e.g., insurance network) and providing information about the identified providers to the user via messages and/or facilitating communication with an identified provider for the user. Furthermore, the provider determination system 104 may include and/or have access to one or more databases. For example, in some embodiments, the provider determination system 104 may be implemented by a plurality of server devices that store, within the one or more databases, provider information and content, insurance information content, user information and content, and/or facilitate querying any of the foregoing information and content to match providers with users based on criteria (e.g., a specialty of a desired provider and/or a location). As is discussed in greater detail below, in some embodiments, the provider determination system 104 may receive messages (e.g., SMS messages) from the client device 102 via the application 112, and based on the received messages, the provider determination system 104 may ultimately provide via a message (e.g., an SMS message) to the client device 102 including information about providers within a user's provider network and based on information (e.g., location information) received from the user and/or accessed by the provider determination system 104.

The third-party systems 114 may include additional systems that interface with the client device 102 and the provider determination system 104. For example, in some embodiments, the third-party systems 114 may include text messaging application programming interfaces ("APIs") (e.g., TWILIO®, PLIVIO®, TELEGRAM® API, TRUE-DIALOG, etc.) and/or natural language processing ("NLP") systems (e.g., DIAGLOGFLOW®, CONVERSABLE®, CHATFUEL®, MANYCHAT®, etc.). In one or more embodiments, the third-party systems 114 may receive messages from the client device 102 and may push the messages to additional third-party systems 114 and/or the provider determination system 104. In additional embodiments, as is described in further detail below, the third-party systems 114 may categorize received messages according communication types before eventually pushing the messages to the provider determination system 104. In some embodiments, while categorizing the received messages, the third-party systems 114 may at least partially process and derive meaning from received messages (e.g., human and/or natural language input).

FIGS. 2A-2F illustrate a sequence-flow diagram 200 showing various acts of client device 102 and the provider determination system 104, in accordance with various embodiments of facilitating communications between client devices and the provider determination system 104. The client device 102, the third-party systems 114, and the provider determination system 104 shown in FIGS. 2A-2F may be example embodiments of the client device 102, the third-party systems 114, and the provider determination system 104 described in regard to FIG. 1.

Figure 2A:
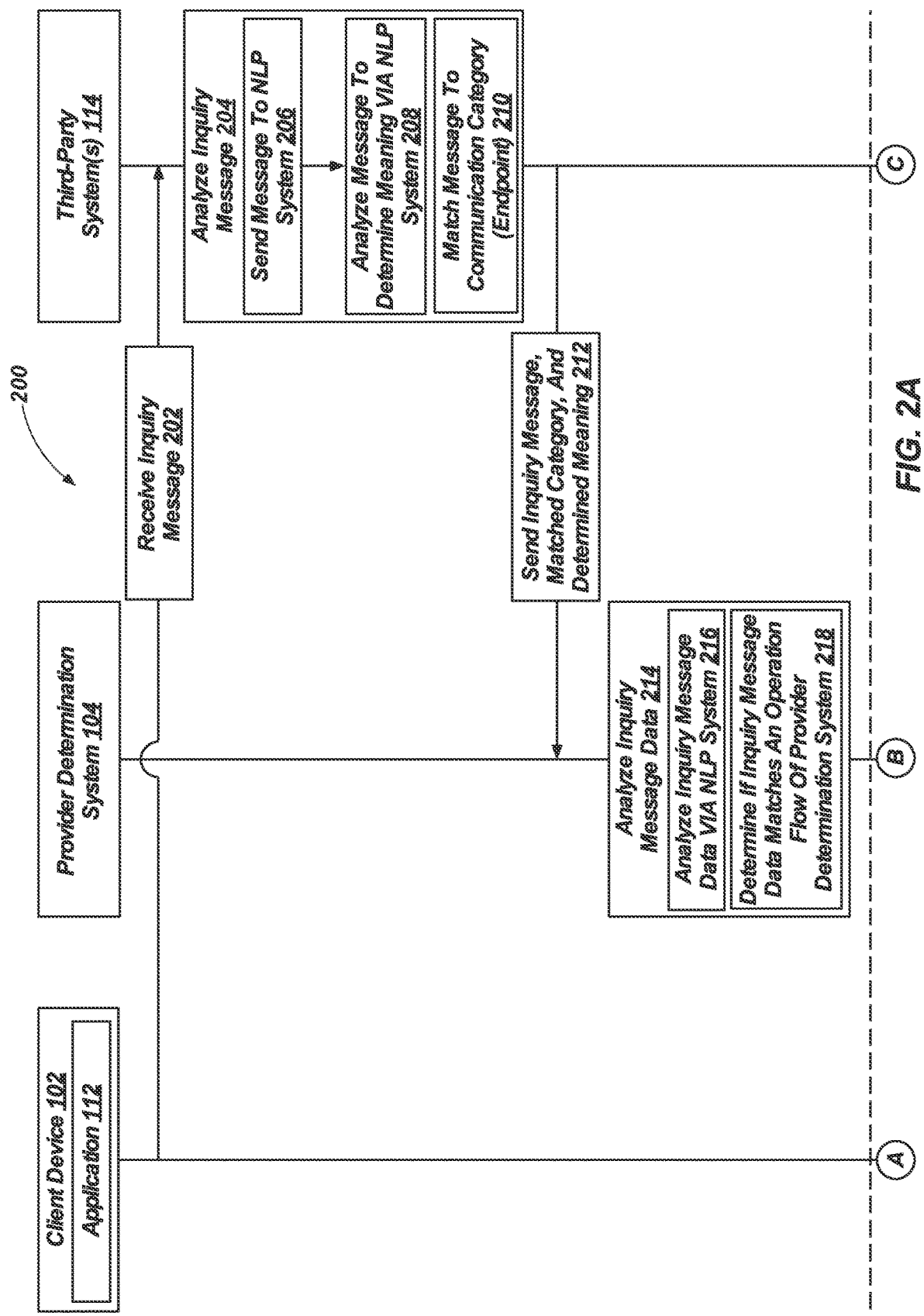

As shown in act 202 of FIG. 2A, in some embodiments, the one or more of the third-party systems 114 receives an inquiry message from the client device 102. As briefly mentioned above, a type of the inquiry message may be at least partially dependent on the client device 102 and/or the application 112 utilized to create the inquiry message. For example, in some embodiments, the message may include a low-data message (e.g., an SMS message, an MMS message, an iMessage, etc.). In other embodiments, the message may include an audio and/or video recording. In further embodiments, the message may include an email, a message received via a website interface, a message received via a messenger, etc.

In some embodiments, the inquiry message may include a request related to services provided by the provider determination system 104. For instance, the inquiry message may include a request for information for providers with a user's provider network and/or the inquiry message may include a request to be put in contact with a provider. As a non-limiting example, the inquiry message may include the word "doctor."

Furthermore, the one or more third-party systems 114 may receive the inquiry message from the client device 102 and/or application 112 of the client device 102 via a network (e.g., a cellular network). In other words, upon detecting a user interaction (e.g., textual inputs, audio inputs, video inputs, etc.) inputting an inquiry message and addressing the inquiry message to the provider determination system 104, the client device 102 and/or application 112 of the client device 102 may provide the inquiry message to the third-party systems 114. For example, the third-party systems 114 and the provider determination system 104 may have a routing number or identifier (e.g., a telephone number or a short number) to which the client device 102 may send the inquiry message. As an illustration, the user 110 may use the client device 102 to send an SMS message to the third-party systems 114 and the provider determination system 104. As noted above, the third-party systems 114 may include messaging application programming interfaces ("APIs") (e.g., TWILIO®, PLIVIO®, TELEGRAM® API, TRUEDIA-LOG, etc.) and/or natural language processing ("NLP") systems (e.g., DIAGLOGFLOW®, CONVERSABLE®, CHATFUEL®, MANYCHAT®, etc.).

In view of the foregoing, the one or more third-party systems 114 may receive the inquiry message via one or more messaging APIs. For instance, the routing number or identifier may be associated with the one or more messaging APIs. Upon receiving the inquiry message, the one or more third-party systems 114 analyzes the inquiry message, as shown in act 204 of FIG. 2A. In some embodiments, analyzing the inquiry message may include pushing a message to an API of an NLP system of the one or more third-party systems 114, as shown in act 206 of FIG. 2A.

Utilizing the NLP system, the one or more third-party systems 114 may analyze the inquiry message to identify content from the inquiry message and to determine a meaning of the identified content of the message, as shown in act 208 of FIG. 2A. In particular, as noted above in regard to FIG. 1, the one or more third-party systems 114 may include one or more NLP systems (e.g., DIAGLOGFLOW®) for processing and deriving meaning from human and/or natural language input (e.g., the inquiry message). For example, the one or more third-party systems 114 may include any NLP system known in the art. Accordingly, the one or more third-party systems 114 may analyze the inquiry message via the NLP system to determine and derive meanings of the identified content of the inquiry message.

In one or more embodiments, the one or more third-party systems 114 may analyze the inquiry message and determine and derive meanings of the identified content of the message to determine whether the inquiry message includes key words and/or phrases that may correlate to services offered by the provider determination system 104 and/or to a communication category designated by the provider determination system 104. As a few non-limiting examples, the one or more third-party systems 114 may determine if inquiry message includes one or more of the following key words and/or phrases and/or words and/or phrases that may be related to the following words and/or phrases: "doctor," "provider," heart doctor," "need a doctor," "doctor please," "where is the closest general practitioner," "medical," "medical services," etc. In some embodiments, determining whether the inquiry message includes key words and/or phrases may include querying at least one word dictionary to identify whether determined and derived meaning of the identified content of the message includes and/or is related to the key words and/or phrases.

Based on the determined and derived meaning of the identified content of the inquiry message and/or any identified key words and/or phrases, the one or more third-party systems 114 matches (e.g., map) the inquiry message to a communication category (e.g., endpoint) designated by the provider determination system 104, as shown in act 210 of FIG. 2A. In other words, the one or more third-party systems 114 may assign an identifier to the inquiry message based on the content of the inquiry message. For instance, the one or more third-party systems 114 may match the inquiry message to an initiating category, a location information category, a provider type category, a selection category, a termination category, a referral category, recommendation category, a schedule category, or an unknown category of the provider determination system 104.

As a non-limiting example, the message may be matched to an initiating category if it is the inquiry message sent to the one or more third-party systems 114 if the initial message received within a communication session and if the message includes a generic phrase such as "doctor" or "find doctor." Additionally, the inquiry message may be matched to the location information category if the inquiry message includes an address, city, GPS coordinates, or any other type of location information. Moreover, the inquiry message may be matched to a specialty provider category if the inquiry message includes key words such as "cardiologist" or "heart doctor." Furthermore, the inquiry message may be matched to the termination category if the inquiry message includes the key words or phrases such as "stop" or "stop sending me messages." Additionally, the inquiry message may be matched to the referral category if the inquiry message includes the key words or phrases such as "referral" or "refer." Moreover, the inquiry message may be matched to the recommendation category if the inquiry message includes the key words or phrases such as "recommend" or "recommendation." Furthermore, the inquiry message may be matched to the schedule category if the inquiry message includes the key words or phrases such as "schedule" or "appointment" Likewise, the inquiry message may be matched with the unknown category if the inquiry message does not include any derived meaning and/or key words and phrases that match a defined communication category of the provider determination system 104. Accordingly, the one or more third-party systems 114 may effectively filter out messages that may not be related to any services offered by the provider determination system 104. For instance, the unknown category may include messages identified as junk and/or spam and/or unrelated messages. In some embodiments, the one or more third-party systems 114 may not provide the messages categorized within the unknown category to the provider determination system 104. As is discussed in greater detail below, matching the inquiry message to a communication category may assist the provider determination system 104 in identifying a logic flow to utilize when communicating with the client device. For instance, the provider determination system 104 may selected a logic flow to implement based on the matched communication category.

In response to matching (e.g., mapping) the inquiry message to a communication category (e.g., endpoint) of the provider determination system 104, the one or more third-party systems 114 may provide (e.g., push) the inquiry message, the matched category (e.g., endpoint) and/or the determined and derived meanings of the message (referred to herein collectively as "inquiry message data") to the provider determination system 104, as shown in act 212 of FIG. 2A. In some embodiments, the one or more third-party systems 114 may provider the inquiry message data to the provider determination system 104 via any of the networks and communication methods described herein.

Upon receiving the inquiry message data from the one or more third-party systems 114, the provider determination system 104 may further analyze the inquiry message data, as shown in act 214 of FIG. 2A. In some embodiments, analyzing the inquiry message data may include analyzing the inquiry message data via a machine learning NLP system (e.g., a second NLP system), as shown in act 216 of FIG. 2A. Additionally, analyzing the inquiry message data may include determining if the inquiry message data correlates to the service offered by the provider determination system 104, as shown in act 218 of FIG. 2A. Each of the foregoing analyses is described in greater detail below.

As noted above, in some embodiments, analyzing the inquiry message data may include analyzing the inquiry message data via a machine learning NLP system (e.g., NLTK PYTHON®). For instance, one or more NLP processes of the machine learning NLP system may include machine learning and/or deep learning techniques that include providing training corpora to a matching learning algorithm or neural network to train a machine to aid or perform the natural language processing. In some embodiments, the provider determination system 104 may analyze the inquiry message data utilizing one or more of regression models (e.g., a set of statistical processes for estimating the relationships among variables), classification models, and/or phenomena models. Additionally, the machine-learning models may include a quadratic regression analysis, a logistic regression analysis, a support vector machine, a Gaussian process regression, ensemble models, or any other regression analysis. Furthermore, in yet further embodiments, the machine-learning models may include decision tree learning, regression trees, boosted trees, gradient boosted tree, multilayer perceptron, one-vs-rest, Naïve Bayes, k-nearest neighbor, association rule learning, a neural network, deep learning, pattern recognition, or any other type of machine-learning.

For example, the provider determination system 104 may apply one or more of the above described machine learning techniques to the inquiry message data in conjunction with any subsequent or earlier messages sent to the client device (discussed below) and any response messages received from the client device. In other words, the provider determination system 104 may apply one or more of the above described machine learning techniques to the feedback loop of the communication session with the client device. Furthermore, by applying the one or more machine-learning techniques to the inquiry message data, any subsequent or earlier messages sent to the client device, and any response messages received from the client device, the provider determination system 104 may match the inquiry message data with an operation flow and/or a logic flow (e.g., a communication flow) of the provider determination system 104, as shown in act 218 of FIG. 2A. In some embodiments, an operation flow and/or logic of the provider determination system 104 may include flows of actions that are utilized in different scenarios. For instance, a first operation flow may include a decision tree utilized when a user initiates a communication session with the provider determination system 104. Another operation flow may include a decision tree utilized when a user provides location data, the user provides a provider specialty, or the user selects a provider from a list. In view of the foregoing, the operation flows may be related to services offered by the provider determination system.

As a non-limiting example, the provider determination system 104 may utilize the feedback loop of the communication session (e.g., back and forth messages, trial and error, etc.) to train the machine-learning models to match the message data (e.g., the inquiry message data) with an operation flow and/or a logic flow of the determination system 104. In other words, via the machine learning model techniques, the provider determination system 104 may learn correlations between message data (e.g., key words, key phrases, etc.) and operation flows and/or logic flows of the provider determination system 104. Put another way, the provider determination system 104 may learn the relationship between the message data and the operation flows and/or the logic flows of the provider determination system 104. For example, as will be understood in the art, for a given set of input values (e.g., the message data (i.e., the inquiry message, the matched category data and/or the determined and derived meanings of the inquiry message)) of a received message, the provider determination system 104 is expected to produce the same output values (i.e., correct operation flows and/or correct logic flows) as would be actually understood by a human operator. In particular, the machine learning models are trained via supervised learning, as is known in the art. After a sufficient number of iterations, the machine learning models become trained machine-learning models. In some embodiments, the machine learning models may also be trained on historical data (e.g., claim data, message data, chat data, etc.) from previous messages and/or claims related to the operations of the provider determination system 104.

As noted above, based on the analysis performed by the provider determination system 104, the provider determination system 104 determines whether the inquiry message data matches an operation flow of the provider determination system 104, as shown in act 218 of FIG. 2A. For instance, the provider determination system 104 may determine whether the inquiry message data matches an operation flow of the provider determination system 104. As a few non-limiting examples, the operations flows of the provider may include providing information about doctors within a geographical area, providing a list of doctors covered under the user's provider network or company's network, providing information about a specific doctor, etc.

In some embodiments, analyzing the inquiry message data further includes determining a phone number and/or user account associated with the inquiry message data and/or client device 102. For example, the provider determination system 104 may analyze the inquiry message data to determine a provider network, an insurance, an employer, or a network account associated with the inquiry message data. For instance, the provider determination system 104 may analyze the inquiry message data to identify a unique identifier included with the inquiry message (e.g., a telephone number, messenger account, tag, etc.). In some embodiments, the provider determination system 104 may identify a unique identifier included in the body of the inquiry message data (e.g., a unique identifier inputted by a user). In additional embodiments, the provider determination system 104 may analyze the inquiry message data (e.g., analyze metadata of the inquiry message) to determine a unique identifier (e.g., telephone number, messenger account, handle, tag, email address, etc.) from which the message originated. Furthermore, the provider determination system 104 may query a unique identifier database to determine a provider network, an insurance network, an employer, an insurance group, or other network account associated with the unique identifier. In alternative embodiments, the unique identifier may be a number to which the inquiry message was sent. For instance, each provider network supported by the provider determination system 104 may have a unique identifier (e.g., telephone number or short code) associated therewith. As a result, merely by receiving the inquiry message at a particular telephone number may inform the provider determination system 104 of the particular provider network.

Furthermore, the provider determination system 104 may analyze the inquiry message data to determine a suitable method to communicate with the client device 102. For example, the provider determination system 104 may analyze the inquiry message data to determine a type of the inquiry message (e.g., SMS message, EMS message, MMS message, email, audio message, video message, etc.), and based on the type of the inquiry message, the provider determination system 104 may determine (e.g., conclude) to communicate with the client device 102 via a same type of message. Although, the provider determination system 104 is described herein as analyzing the inquiry message data to determine a unique identifier and/or a suitable method to communicate with the client device 102, the present disclosure is not so limited, and, in some embodiments, one or more of the third-party systems 114 may perform any of the above-described analyses.

Upon matching the inquiry message data to an operation flow and/or logic flow of the provider determination system 104 and determining a type of message with which to communicate with the client device 102, the provider determination system 104 may initiate the operation flow and/or logic flow. In some embodiments, the provider determination system 104 may initiate the operation flow and/or logic flow at a beginning of the operation flow and/or logic flow. In additional embodiments, the provider determination system 104 may initiate the logic flow at an intermediate point depending on the where the inquiry message data places a communication session within the operation flow and/or logic flow. As a non-limiting example, if the inquiry message includes the term "doctor," the provider determination system 104 may initiate a logic flow that requests a location, then requests a provider types, then provides a list of providers matching the location and the provider type, and then provides information related to the selected provider. In some embodiments, each of the foregoing-listed steps has its own distinct logic flow.

For example, in some embodiments, initiating a logic flow, includes generating a request for location information (e.g., city and/or zip code) ("referred to hereinafter as "location request"), as shown in act 220 of FIG. 2B. The provider determination system 104 may generate the location request to match the determined type (e.g., communication type (e.g., email, SMS message, audio message, video message, etc.)) of the received inquiry message. For instance, in some embodiments, the location request may include an SMS message. In other embodiments, the location request may include any of the other types of messages described above. In one or more embodiments, the provider determination system 104 may generate the location request or any other message described herein via a message generator of a dialogue system (e.g., a Chatbot architecture) (described in greater detail below in regard to FIG. 3) of the provider determination system 104. For instance, the message generator of the dialogue system (e.g., a Chatbot architecture) of the provider determination system 104 may include a plurality of pre-defined template messages with placeholders that the message generator can customize based on received messages. Furthermore, the provider determination system 104 may generate the location request or any other message described herein based on predictions made by a dialogue manager (described in greater detail below in regard to FIG. 3) of the provider determination system 104. For instance, the dialogue manager may include models for predicting next messages (e.g., messages to generate) based on previous messages (e.g., received messages).

In one or more embodiments, the provider determination system 104 may generate the location request to include textual elements requesting that the user input a textual response (e.g., a text message) with location information. In additional embodiments, the provider determination system 104 may generate the request message to include a message requesting permission to access the GPS location of the client device 102. In some embodiments, the message generator of the provider determination system 104 may include a natural language generation ("NLG") system for generating and/or customizing messages/requests to provide to the client device 102 in response to receiving messages (e.g., the inquiry message). In other words, the provider determination system 104 may generate natural language messages from a machine representation system such as a knowledge base and/or a logical form. Furthermore, the provider determination system 104 may utilize the NLG system to generate the location request.

Figure 2B:
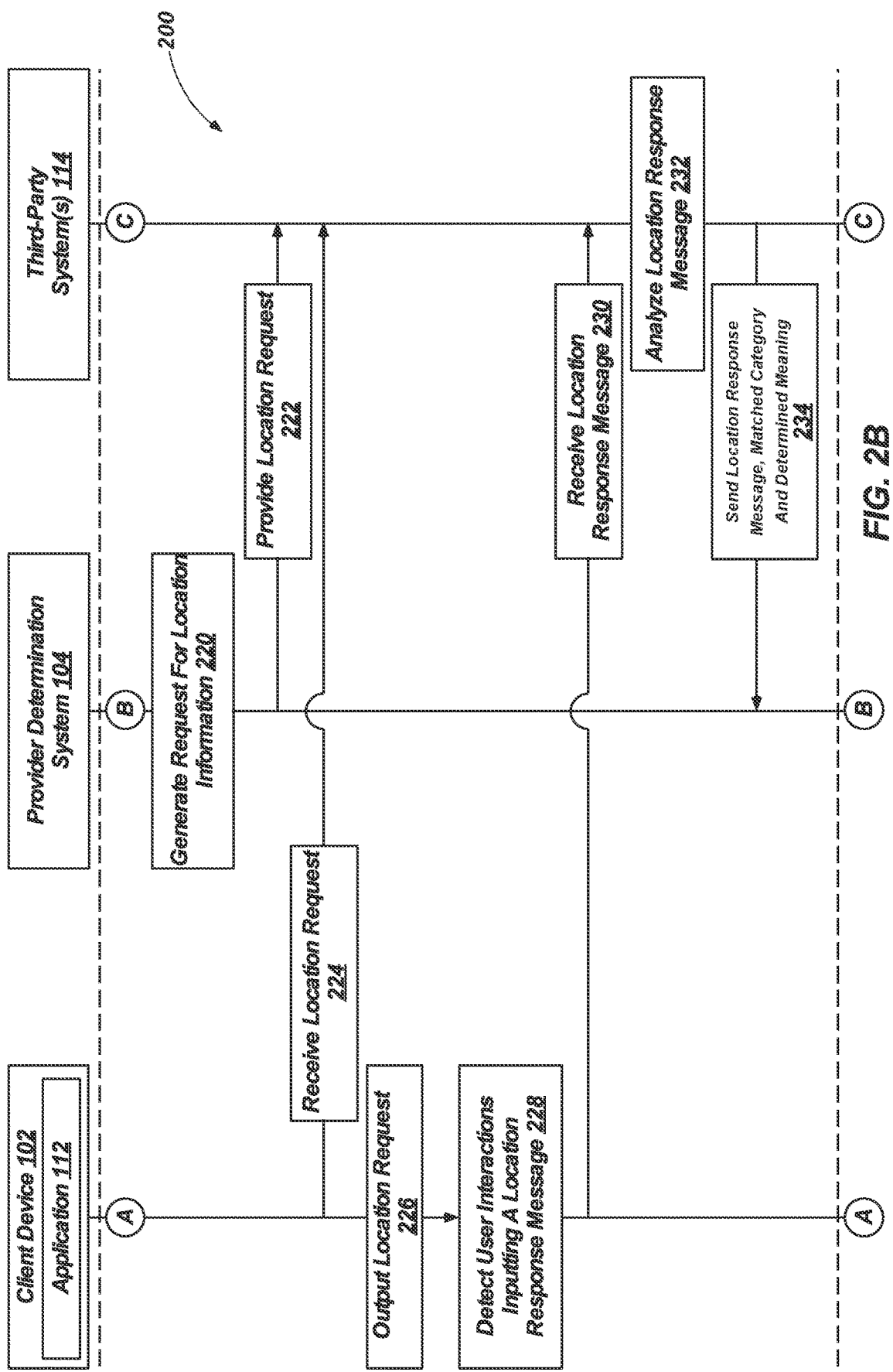

Upon generating the location request, the provider determination system 104 provides the location request to the one or more third-party systems 114 (e.g., the messaging API of the third-party systems 114) for relay to the client device 102, as shown in act 222 of FIG. 2B. The provider determination system 104 may provide the location request to the one or more third-party systems 114 via any of the networks and communication methods described herein.

Upon receiving the location request from the provider determination system 104, the one or more third-party systems 114 (e.g., the messaging API) relays the location request to the client device 102, as shown in act 224 of FIG. 2B. The one or more third-party systems 114 (e.g., the messaging API) may provide the location request to the client device 102 via any of the networks and communication methods described herein.

In response to receiving the location request, the application 112 and/or client device 102 outputs the location request, as shown in act 226 of FIG. 2B. For example, in some embodiments, the application 112 of the client device 102 may display the communication as a message within the application 112 (e.g., as a text message). Additionally, in one or more embodiments, the application 112 of the client device 102 may display the communication as a notification within the application 112. Furthermore, the application 112 of the client device 102 may display the communication via a graphical user interface (e.g., GUI) of the application 112, as discussed in further detail in regard to FIGS. 4A-4F. Alternatively, as noted above, the client device 102 may display the communication (e.g., a notification) via the operating system of the client device 102 (e.g., as a push notification). In further embodiments, the application 112 and/or client device 102 may output the location request as audio sound (e.g., as audio sound in the case where the client device 102 includes, for example, a smart speaker) and/or as video.

In addition to outputting the location request within the application 112, the application 112 and/or client device 102 detects a user interaction inputting a location response message, as shown in act 228 of FIG. 2B. As used herein, the terms "user interaction" mean a single interaction, or combination of interactions, received from a user by way of one or more input devices (e.g., a touch screen display, a keyboard, a mouse, microphone, camera, etc.) of the client device 102. Furthermore, the user interaction may include one or more of clicking, tapping, or otherwise selecting elements (e.g., letters and/or characters) to include in the message, speaking, and/or capturing video. For example, the application 112 of the client device 102 detects a user interaction inputting a location response message (e.g., a text message) within the application 112 in response to the prompt. In alternative embodiments, the client device 102 detects a user interaction within a notification interface in response to the prompt. In further embodiments, the application 112 and/or client device 102 detects a user interaction including audible sounds and/or initiating capturing a video.

In response to the client device 102 detecting a user interaction inputting a location response message, the one or more third-party systems 114 receives the location response message, as shown in act 230 of FIG. 2B. For example, the one or more third-party systems 114 may receive the location response message from the client device 102 and/or application 112 of the client device 102 via a network (e.g., a cellular network). In other words, upon detecting a user interaction inputting the location response message, the client device 102 and/or application 112 of the client device 102 may provide the location response message to the one or more third-party systems 114. Furthermore, the one or more third-party systems 114 may receive the location response message via any of the manners described above in regard to act 202 of FIG. 2A.

Additionally, upon receiving the location response message, the one or more third-party systems 114 analyzes the location response message, as shown in act 232 of FIG. 2B. For example, the one or more third-party systems 114 may analyze the location response message via any of the manners, methods, and system described above in regard to acts 204-210 of FIG. 2A to determine and derive a meaning of the location response message and match the location response message to a communication category (e.g., the location information category) of the provider determination system 104.

Upon determining and deriving a meaning of the location response message and matching (e.g., mapping) the location response message to a communication category of the provider determination system 104, the one or more third-party systems 114 may provide (e.g., push) the location response message, the matched category (e.g., endpoint) data, and/or the determined and derived meanings of the location response message (referred to hereinafter collectively as "location message data") to the provider determination system 104, as shown in act 234 of FIG. 2B. In some embodiments, the one or more third-party systems 114 may provide the location message data to the provider determination system 104 via any of the networks and communication methods described herein.

Figure 2C:
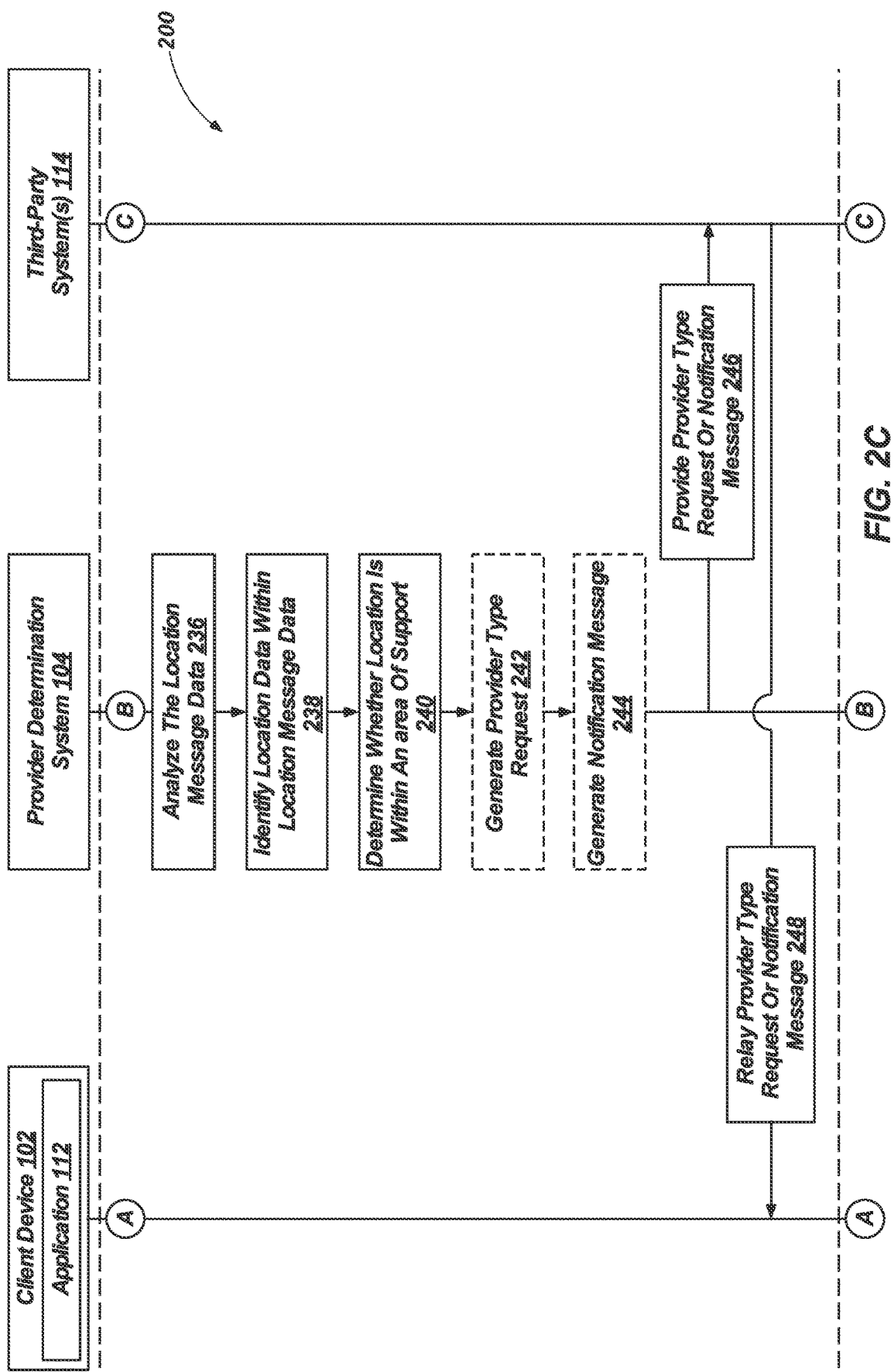

Upon receiving the location message data from the one or more third-party systems 114, the provider determination system 104 may further analyze the location message data, as shown in act 236 of FIG. 2C. For instance, the provider determination system 104 may analyze the location message data via any of the manners, methods, and systems described above in regard to acts 214-218 of FIG. 2A. The provider determination system 104 may analyze the location message data via the foregoing manners to identify location data within location message data, as shown in act 238 of FIG. 2C. For instance, provider determination system 104 may analyze the location message data to identify one or more of an address, a zip code, a city, a state, a GPS location, etc.

Based on the identified location data, the provider determination system 104 determines whether a location identified within the identified location data is within an area of support of the provider determination system 104, as shown in act 240 of FIG. 2C. In particular, the provider determination system 104 queries a provider database of the provider determination system 104 to determine whether the identified location matches (e.g., falls within) an area (e.g., geographical are) that the provider determination system 104 is currently supporting.

If the provider determination system 104 determines that the identified location of the identified location data is within an area of support of the provider determination system 104, the provider determination system 104 generates a provider type request (e.g., a provider type request message), as shown in act 242 of FIG. 2B. If, on the other hand, the provider determination system 104 determines that the identified location of the identified location data is not within an area of support of the provider determination system 104, the provider determination system 104 generates notification message to the user to notify the user that the identified location is not currently supported by the provider determination system 104, as shown in act 244 of FIG. 2B. Each of the foregoing actions is described in further detail below.

As noted above, if the provider determination system 104 determines that the identified location of the identified location data is within an area of support of the provider determination system 104, the provider determination system 104 generates a provider type request. For example, the provider determination system 104 may generate the provider type request to include a request for the user to identify a specialty of a desired provider (e.g., doctor), a type of desired doctor, and/or a type of desired treatment. The provider determination system 104 may generate the provider type request via any of the manners described above in regard to 220 of FIG. 2B.

As also mentioned above, if the provider determination system 104 determines that the identified location of the identified location data is not within an area of support of the provider determination system 104, the provider determination system 104 generates a notification message to the user to notify the that the identified location is not currently supported by the provider determination system 104. In some embodiments, the notification message may include a message redirecting the user to a provider service (e.g., the insurance carrier and/or employer) for information. The provider determination system 104 may generate the notification message via any of the manners described above in regard to 220 of FIG. 2A.

Regardless of whether the provider determination system 104 generates the provider type request according to act 242 or the notification message of act 244, the provider determination system 104 provides the provider type request or the notification message to the one or more third-party systems 114 (e.g., the messaging API) for relay to the client device 102, as shown in act 246 of FIG. 2C. The provider determination system 104 may provide the provider type request or the notification message to the one or more third-party systems 114 via any of the networks and communication methods described herein.

Upon receiving the provider type request or the notification message from the provider determination system 104, the one or more third-party systems 114 (e.g., the messaging API) relays the provider type request or the notification message to the client device 102, as shown in act 248 of FIG. 2C. The one or more third-party systems 114 (e.g., the messaging API) may provide the provider type request or the notification message to the client device 102 via any of the networks and communication methods described herein.

Figure 2D:
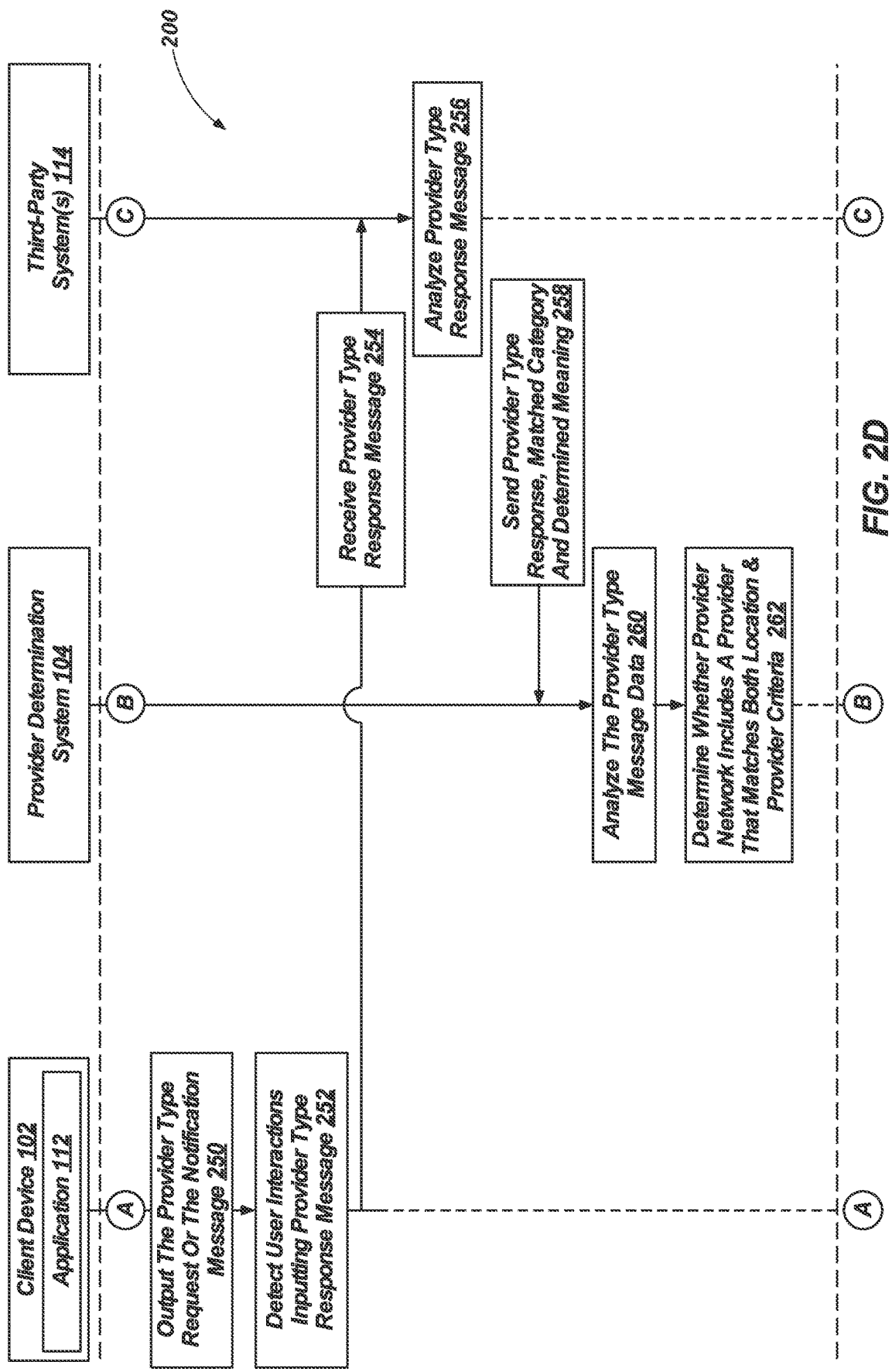

In response to receiving the provider type request or the notification message, the application 112 and/or client device 102 outputs the provider type request or the notification message, as shown in act 250 of FIG. 2D. For instance, the application 112 and/or client device 102 may output the provider type request or the notification message via any of the methods described above in regard to act 226 of FIG. 2B. For example, the application 112 and/or client device 102 may output the provider type request or the notification message as a text message, notification, email, audio message, video message, etc.

In response to outputting the provider type request, the application 112 and/or client device 102 detects a user interaction inputting a provider type response message, as shown in act 252 of FIG. 2D. Furthermore, the types of user interactions may include any of the user interactions described above in regard to act 228 of FIG. 2B. In some embodiments, the provider type response message includes an indication of a doctor specialty. As a few non-limiting examples, the provider type response message may include one or more of the following messages "heart doctor," "cardiologist," "heart treatment," "podiatrist," "foot doctor," "back pain," etc.

In response to the client device 102 detecting a user interaction inputting a provider type response message, the one or more third-party systems 114 receives the provider type response message, as shown in act 254 of FIG. 2D. For example, the one or more third-party systems 114 may receive the provider type response message from the client device 102 and/or application 112 of the client device 102 via a network (e.g., a cellular network). In other words, upon detecting a user interaction inputting the provider type response message, the client device 102 and/or application 112 of the client device 102 may provide the provider type response message to the one or more third-party systems 114. Furthermore, the one or more third-party systems 114 may receive the provider type response message via any of the manners described above in regard to act 202 of FIG. 2A.

Additionally, upon receiving the provider type response message, the one or more third-party systems 114 analyzes the provider type response message, as shown in act 256 of FIG. 2D. For example, the one or more third-party systems 114 may analyze the provider type response message via any of the manners, methods, and system described above in regard to acts 206-210 of FIG. 2A to determine and derive a meaning of the provider type response message and match the provider type response message to a communication category (e.g., the provider type category) of the provider determination system 104.

Upon determining and deriving a meaning of the provider type response message and matching (e.g., mapping) the provider type response message to a communication category of the provider determination system 104, the one or more third-party systems 114 may provide (e.g., push) the provider type response message, the matched category (e.g., endpoint) data, and/or the determined and derived meanings of the provider type response message (referred to hereinafter collectively as "provider type message data") to the provider determination system 104, as shown in act 258 of FIG. 2D. In some embodiments, the one or more third-party systems 114 may the (referred to hereinafter collectively as "provider type message data") to the provider determination system 104 via any of the networks and communication methods described herein.

Upon receiving the provider type message data from the one or more third-party systems 114, the provider determination system 104 may further analyze the provider type message data, as shown in act 260 of FIG. 2D. For instance, the provider determination system 104 may analyze the provider type message data via any of the manners, methods, and systems described above in regard to acts 214-218 of FIG. 2A. The provider determination system 104 may analyze the provider type message data via the foregoing manners to identify a provider specialty, a provider type, or a desired treatment (referred to hereinafter collectively as "provider criteria") identified within provider type message data.

In response to analyzing the provider type message data and identifying provider criteria within the provider type message data, the provider determination system 104 determines whether the provider network associated with the client device 102 (e.g., the unique identifier described above in regard to act 218 of FIG. 2A) includes a provider that matches the received provider criteria and the received location data, as shown in act 262 of FIG. 2D. For instance, the provider determination system 104 may query the provider database to determine whether any providers identified in the provider database and within the provider network match both of the provider criteria (e.g., the provider practices in a particular specialty) and the location data. In particular, the provider determination system 104 may query the provider database to search one or more records of providers within the provider database to determine whether, based on the records, any providers identified in the provider database match both of the provider criteria and the location data.

In one or more embodiments, the provider determination system 104 may determine that a provider matches the location data if the provider (e.g., a business address of the provider) falls within a specific radius from the location identified in the location data. In some embodiments, the provider determination system 104 may determine that a provider matches the location data if the provider (e.g., a business address) falls within five miles, ten miles, twenty miles, fifty miles, one hundred miles, etc., of the location identified in the location data. In one or more embodiments, the provider determination system 104 may query/access one or more map (e.g., geographic information) provider systems (e.g., GOOGLE MAPS, APPLE MAPS, etc.) to determine whether the provider falls within the specific radius from the location identified in the location data. In some embodiments, the provider determination system 104 may determine that a provider matches the location data if the provider (e.g., a business address) falls within a distance of the location identified in the location data where the distance is selected by the user. For instance, the distance may be selected via a message or within preferences of the user. As is discussed in further detail below, in some embodiments, the provider determination system 104 may identify providers based on criteria other than or in addition to location data. For example, the provider determination system 104 may identify providers based on current wait time, radius from public transport, etc.

If the provider determination system 104 identifies one or more providers within the provider database that matches both the provider criteria and the location data, the provider determination system 104 generates a provider list message including a list of one or more matching providers, as shown in act 264 of FIG. 2E. If, conversely, the provider determination system 104 does not identify one or more providers within the provider database that matches both the provider criteria and the location data, the provider determination system 104 generates a notice message to notify the user that the provider network of the user does not currently include providers matching the provider criteria and/or the location data, as shown in act 266 of FIG. 2E. Each of the foregoing is described in detail below.

As noted above, if the provider determination system 104 identifies one or more providers within the provider database that matches both the provider criteria and the location data, the provider determination system 104 generates the provider list message to include a list of one or more matching providers, as shown in act 264 of FIG. 2E. For instance, in some embodiments, the provider determination system 104 may generate the provider list message to include at least three matching providers. In some embodiments, the provider determination system 104 may generate the provider list message to include a name of each of the one or more matching providers and a distance from the location identified in the location data. Furthermore, provider determination system 104 may generate the provider list message to include a question asking if the user would like additional details about any of the providers listed in the provider list message and to identify the provider if the user would like additional details.

In some embodiments, the provider list message may list (e.g., rank) the one or more matching providers based on a distance from the location identified in the location data. For instance, a first listed provider may be closest to the location identified in the location data, and a last listed provider may be the farthest from the location identified in the location data. In one or more embodiments, the provider list message may list (e.g., rank) the one or more matching providers based on a curation process performed by the provider determination system 104. For instance, the provider determination system may curate (e.g., select) providers to include within the provider list message based on performance factors. In some embodiments, the performance factors may include one or more of the following: an average wait time, average patient ranking, cost, a number of malpractice claims, an employer preference, etc. Accordingly, in some embodiments, the provider list message may include a curated list of providers. As a result, in some embodiments, a closest provider may not always be listed first.

As mentioned above, if the provider determination system 104 does not identify one or more providers within the provider database that matches both the provider criteria and the location data, the provider determination system 104 generates a notice message to notify the user that their provider network does not currently include providers matching the provider criteria and/or the location data, as shown in act 266 of FIG. 2E. For instance, the provider determination system 104 generates a notice message to include an indication that the user's provider network does not include a provider matching the provider criteria at or near the location identified in the location data. In some embodiments, the notice message may include a request for an input of a different location (e.g., a request to try a different location). In one or more embodiments, the notice message may include a message that the specified provider type is not supported by the provider determination system 104 and a suggestion to contact the provider network directly. In further embodiments, the notice message may include one or more providers meeting the provider criteria while noting that the one or more providers are not near the location identified in the location data. These providers may be identified in the same manner discussed above in regard to acts 262 and 264 of FIGS. 2D and 2E. In additional embodiments, the notice message may include message redirecting the user to the user's insurance provider or health plan. For instance, the notice message may include "We were unable to find providers in your location. Please call 555-555-1234 to speak with a representative for additional options."

Regardless of whether the provider determination system 104 generates the provider list message according to act 264 or the notice message according to act 266, the provider determination system 104 provides the provider list message or the notice message to the one or more third-party systems 114 (e.g., the messaging API) for relay to the client device 102, as shown in act 268 of FIG. 2E. The provider determination system 104 may provide the provider list message or the notice message to the one or more third-party systems 114 via any of the networks and communication methods described herein.

Upon receiving the provider list message or the notice message from the provider determination system 104, the one or more third-party systems 114 (e.g., the messaging API) relays the provider list message or the notification message to the client device 102, as shown in act 270 of FIG. 2E. The one or more third-party systems 114 (e.g., the messaging API) may provide the provider list message or the notice message to the client device 102 via any of the networks and communication methods described herein.

In response to receiving the provider list message or the notice message, the application 112 and/or client device 102 outputs the provider list message or the notice message, as shown in act 272 of FIG. 2E. For instance, the application 112 and/or client device 102 may output the provider list message or the notice message via any of the methods described above in regard to act 226 of FIG. 2B. For example, the application 112 and/or client device 102 may output the provider list message or the notice message as a text message, notification, email, audio message, video message, etc.

In response to outputting the provider list message, the application 112 and/or client device 102 detects a user interaction inputting a provider selection response message, as shown in act 274 of FIG. 2E. Furthermore, the types of user interactions may include any of the user interactions described above in regard to act 228 of FIG. 2B. As a few non-limiting examples, the provider selection response message may include one or more of the following messages "1," one," "[provider's name]," "first," "No," etc.

In response to the client device 102 detecting a user interaction inputting a provider selection response message, the one or more third-party systems 114 receives the provider selection response message, as shown in act 276 of FIG. 2E. For example, the one or more third-party systems 114 may receive the provider selection response message from the client device 102 and/or application 112 of the client device 102 via a network (e.g., a cellular network). In other words, upon detecting a user interaction inputting the provider type response message, the client device 102 and/or application 112 of the client device 102 may provide the provider selection response message to the one or more third-party systems 114. Furthermore, the one or more third-party systems 114 may receive the provider selection response message via any of the manners described above in regard to act 202 of FIG. 2A.

Additionally, upon receiving the provider selection response message, the one or more third-party systems 114 analyzes the provider type response message, as shown in act 278 of FIG. 2E. For example, the one or more third-party systems 114 may analyze the provider selection response message via any of the manners, methods, and system described above in regard to acts 204-210 of FIG. 2A to determine and derive a meaning of the provider selection response message and match the provider selection response message to a communication category (e.g., the selection category or a termination category) of the provider determination system 104.

Upon determining and deriving a meaning of the provider selection response message and matching (e.g., mapping) the provider selection response message to a communication category of the provider determination system 104, the one or more third-party systems 114 may provide (e.g., push) the provider selection response message, the matched category (e.g., endpoint) data, and/or the determined and derived meanings of the provider selection response message (referred to hereinafter collectively as "provider selection message data") to the provider determination system 104, as shown in act 280 of FIG. 2E. In some embodiments, the one or more third-party systems 114 may the provider selection message data to the provider determination system 104 via any of the networks and communication methods described herein.

Figure 2F:
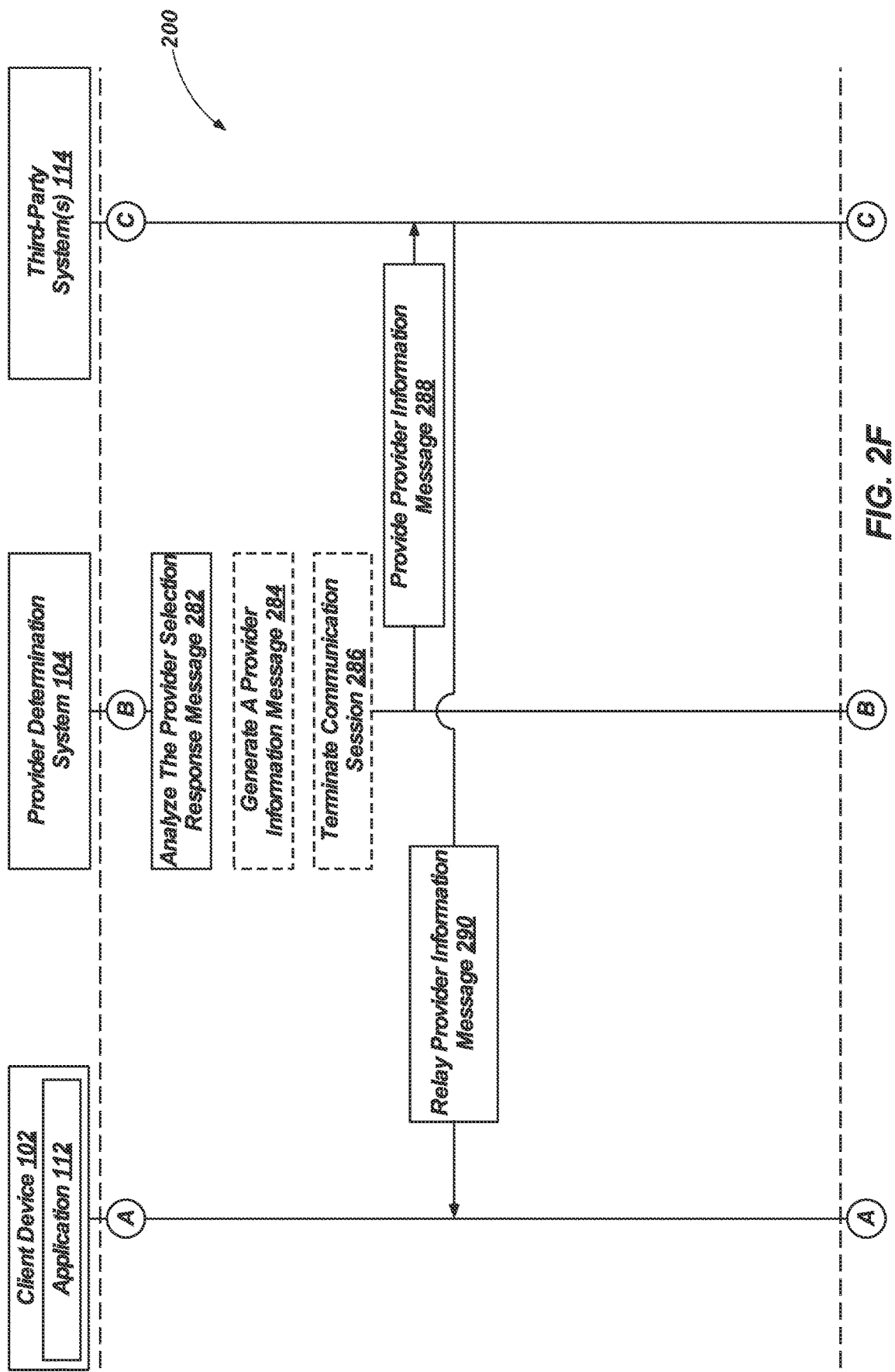

Upon receiving the provider selection message data from the one or more third-party systems 114, the provider determination system 104 may further analyze the provider type message data, as shown in act 282 of FIG. 2F. For instance, the provider determination system 104 may analyze the provider selection message data via any of the manners, methods, and systems described above in regard to acts 214-218 of FIG. 2A. The provider determination system 104 may analyze the provider selection message data via the foregoing manners to match a selection within the provider selection message data to one of the providers listed in the provider list message or to determine that the user wishes to end the communication session. As a non-limiting example, if the provider selection message data includes a provider selection message of "1," the provider determination system 104 determines that the user has selected the first-listed provider of the provider list message and wishes to receive additional information related to the first-listed provider of the provider list message, Conversely, if the provider selection message data includes a provider selection message of "No," the provider determination system 104 determines that the user wishes to terminate the communication session and does not wish to receive any additional information regarding any of the listed providers of the provider list message.

If the provider determination system 104 determines that the user has made a selection of the provider within the provider list message, the provider determination system 104 generates a provider information message, as shown in act 284 of FIG. 2F. If, on the other hand, the provider determination system 104 determines that the user has elected to terminate the communication session, the provider determination system 104 terminates the communicate session, as shown in act 286 of FIG. 2F.

As noted above, if the provider determination system 104 determines that the user has made a selection of the provider within the provider list message, the provider determination system 104 generates a provider information message, as shown in act 284 of FIG. 2E. In one or more embodiments, the provider determination system 104 may generate the provider information message to include one or more of an address of the provider, a phone number of the provider, directions to the provider, a website of the provider, etc. Furthermore, as is discussed in great detail below in regard to FIG. 7, the provider determination system 104 may generate the provider information message to include an offer/option to initiate a further action in regard to the selected provider, such as, for example, initiate a phone call with the provider, initiate a chat with the provider, schedule an appointment with the provider, etc.

Upon generating the provider information message, the provider determination system 104 provides the provider information message to the one or more third-party systems 114 (e.g., the messaging API) for relay to the client device 102, as shown in act 288 of FIG. 2F. The provider determination system 104 may provide the provider information message to the one or more third-party systems 114 via any of the networks and communication methods described herein.

Upon receiving the provider information message from the provider determination system 104, the one or more third-party systems 114 (e.g., the messaging API) relays the provider information message to the client device 102, as shown in act 290 of FIG. 2F. The one or more third-party systems 114 (e.g., the messaging API) may provide the provider information message to the client device 102 via any of the networks and communication methods described herein.

Figure 3:
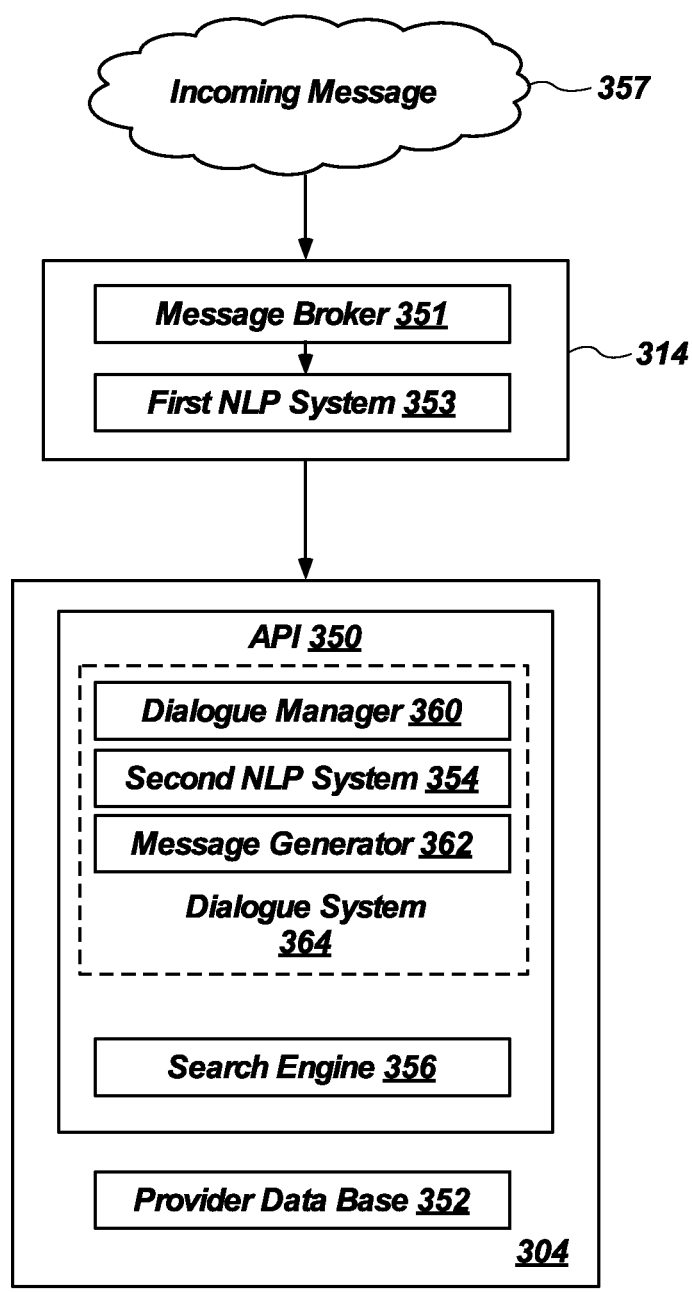
FIG. 3 is a schematic representation of a provider determination system and third-party systems according to one or more embodiments of the present disclosure.

FIG. 3 shows a schematic representation of one or more third-party systems 314 and a provider determination system 304 according to one or more embodiments of the present disclosure. As shown, the one or more third-party systems 314 may include a message broker 351 and a first NLP system 353. As is also shown, the provider determination system 304 may include an API 350 and a provider database 352. As is discussed in great detail below, the provider determination system 304 may utilize the API 350 for interfacing with the one or more third-party systems 314. The API 350 may include a dialogue system 364 and a search engine 356. The dialogue system 364 may be a system (e.g., Chatbot) for engaging in standard conversational patterns. The dialogue system 364 may include a dialogue manager 360, a second NLP system 354, and a message generator 362. The dialogue manager 360 may include one or more models for predicting next actions (e.g., next messages) based on previous actions (e.g., previous messages). The second NLP system 354 may include any of the NLP systems described above in regard to FIGS. 2A-2F. The message generator 362 may include predefined templates with placeholders for generating messages (e.g., text) that will be sent to the message broker 351. In view of the foregoing, the dialogue system 364 may form a Chatbot architecture for engaging in a question/answer session with a user of a client device as part of the provider-finding service for performing the acts of shown in the figures.

During operation, the message broker 351 may receive messages 357 from client devices (e.g., client device 102) according to any of the manners described above in regard to FIGS. 2A-2F. The message broker 351 may push the message 357 to the first NLP system 353, which may process and analyze the message 357 to map the message to a communication category via any of the methods described above in regard to FIGS. 2A-2F.

Upon mapping the message to a communication category, the message broker 351 and/or the NLP system 353 may send the message 357 and any analysis data related to the message 357 to the provider determination system 304. The provider determination system 304 may interact with the message via to the dialogue system 364 (e.g., a Chatbot). In particular, the provider determination system 304 may utilize the dialogue system 364 (e.g., a Chatbot) and specifically the second NLP system 354 of the dialogue system 364 analyze the message via any of the manners described above in regard to FIGS. 2A-2F. For instance, the dialogue system 364 may determine meaning, intent, and/or entities with the second NLP system 354. In some embodiments, as is described above, the processes of the second NLP system 354 may include machine learning and/or deep learning techniques that include providing a training corpora to a matching learning algorithm or neural network to train a machine to aid or perform the natural language processing. Additionally, the dialogue system 364 (e.g., a Chatbot) may manage the message and/or any meanings, intents, and/or entities derived by the second NLP system 354 via the dialogue manager 360. For example, the dialogue manager 360 of the dialogue system 364 (e.g., a Chatbot) may include models for predicting nest actions (e.g., messages) based on previous actions (e.g., messages). Moreover, the dialogue system 364 (e.g., a Chatbot) may generate messages to send to the client device as part of the provider-finding services described herein for performing the acts of FIGS. 2A-2E. Furthermore, the provider determination system 304 may query the provider database 352 via any of the manners described above in regard to FIGS. 2A-2F to match providers, match locations, generate lists of providers, etc.

FIGS. 4A-4F illustrate a flow of user interfaces including features of the environment 100 according to an embodiment of the present disclosure. As will be described in more detail below, the components of the environment 100 as described in regard to FIGS. 1A-3 may provide, alone and/or in combination with the other components, one or more graphical user interfaces ("GUIs"). A GUI typically includes one or more display regions and active/activatable regions. As used in this disclosure, a display region is a region of a GUI which displays information to a user. An activatable region is a region of a GUI, such as a button, slider, or a menu, which allows the user to take some action with respect to the GUI (e.g., if manipulated). Some display regions are also activatable regions in that the activatable regions display information and enable some action that may be taken by a user. In a contact-sensitive GUI, contacting a contact-sensitive area associated with an activatable region may activate that region (e.g., selecting a GUI button). Activatable regions may be displayed as GUI elements/objects, for example, buttons, sliders, selectable panes, menus, etc., all of various shapes and sizes. In particular, the components (e.g., the activatable regions of the GUI) may allow a user 110 to interact with a collection of display elements for a variety of purposes. In particular, FIGS. 4A-4F and the description that follows illustrate various example embodiments of the user interfaces and features that are in accordance with one or more embodiments of the present disclosure.

Figure 4C:
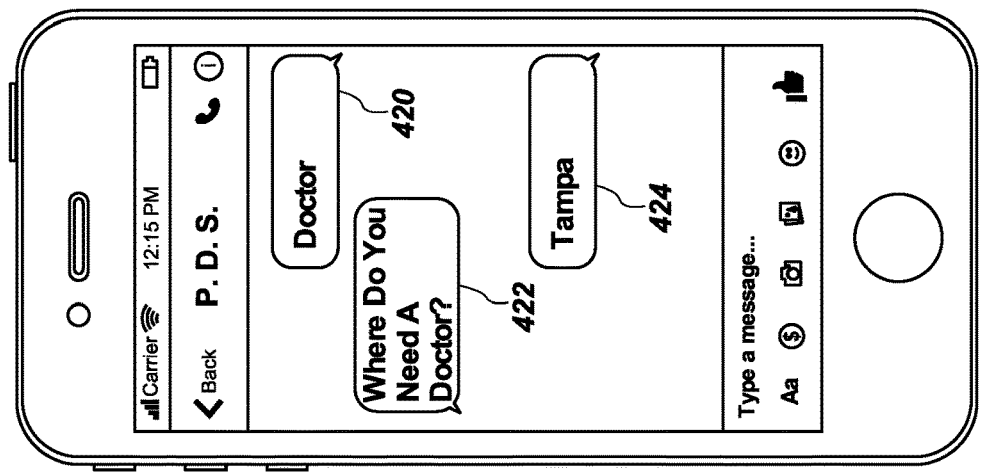
FIGS. 4A-4F illustrate a plurality of schematic representations of graphical user interfaces utilized to communicate with the provider determination system to one or more embodiments of the present disclosure.
Figure 4B:
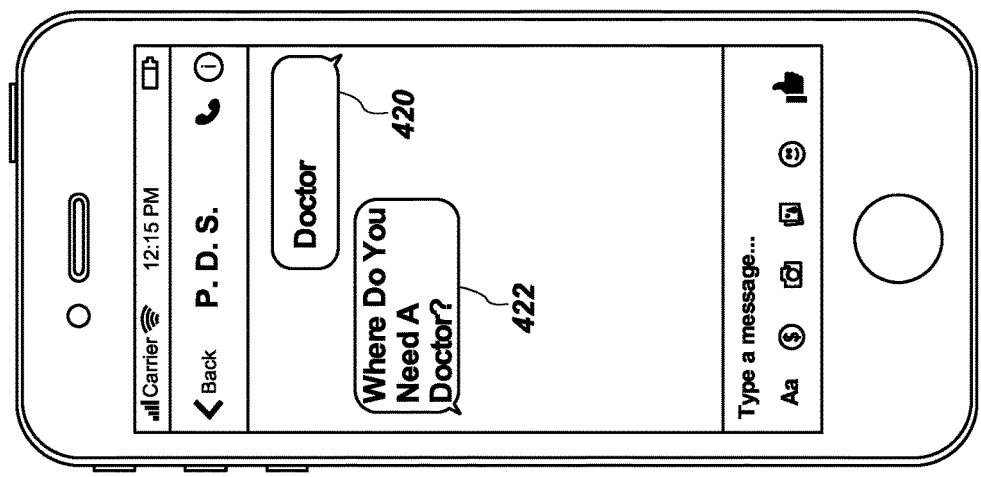
Figure 4A:
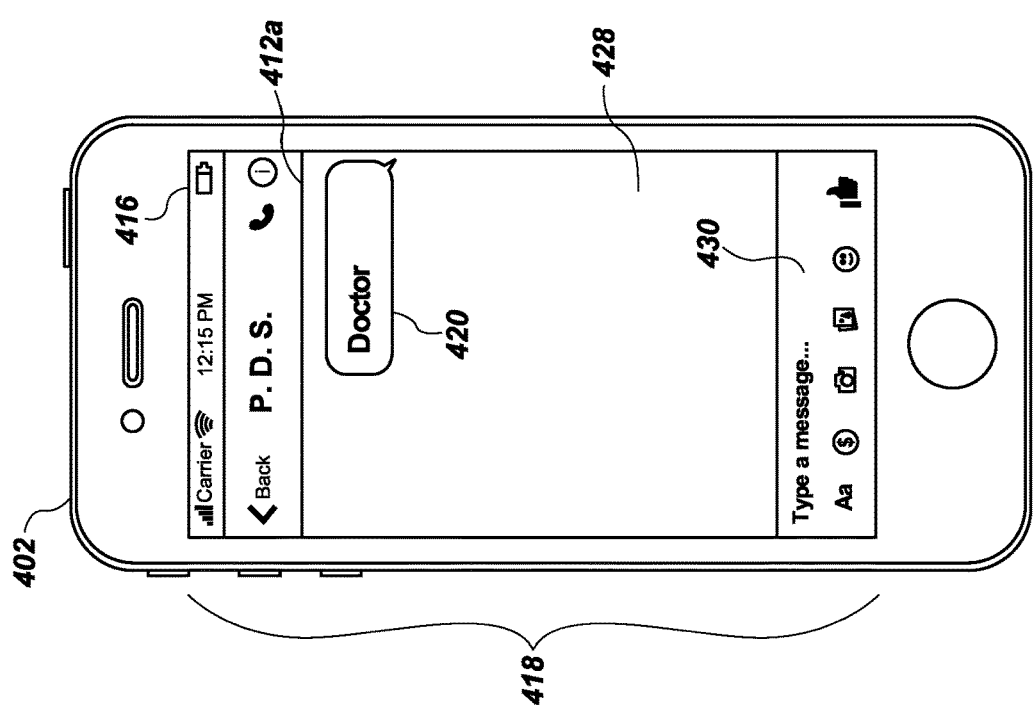

For example, FIG. 4A illustrates a client device 402 of a provider determination system 104 user (e.g., the user 110 of FIG. 1) that may implement one or more of the components or features of the environment 100. As shown in FIG. 4A, in some embodiments, the client device 402 is a handheld device, such as a mobile phone device (e.g., a smartphone). As used herein, the term "handheld device" refers to a device sized and configured to be held/operated in a single hand of the user 110 and/or worn and operated by one or more hands of the user 110. In additional or alternative examples, however, any other suitable computing device, such as, but not limited to, a tablet device, larger wireless device, laptop or desktop computer, a personal digital assistant device, and/or any other suitable computing device may perform one or more of the processes and/or operations described herein.

The client device 402 includes a touch screen display 416 that may display user interfaces. Furthermore, the client device 402 receives and/or detects user input via the touch screen display 416. As used herein, a "touch screen display" refers to the display of a touch screen device. In one or more embodiments, a touch screen device may be the client device 402 with at least one surface upon which a user 110 may perform touch gestures (e.g., a laptop, a tablet computer, a personal digital assistant, a media player, a mobile phone, etc.). Additionally or alternatively, the client device 402 may include any other suitable input device, such as a touch pad or those described below with reference to FIG. 8.

FIGS. 4A-4F show example content of communication messages (e.g., low data messages) having natural language (e.g., without specific commands). As shown in FIG. 4A, the touch screen display 416 of the client device 402 displays a messaging application GUI 412a. The messaging application GUI 412a displays a communication thread GUI 418 showing communications (e.g., messages) between the client device 402 and the provider determination system 104. Furthermore, the communication thread GUI 418 may include a common window 428 for displaying messages from both of the user and the provider determination system 104. Moreover, the communication thread GUI 418 may include an input area 430 for adding messages to the common window 428. The communication thread GUI 418 may further include a plurality of selectable elements for sending communications from the user and for closing the communication thread GUI 418.

As noted above, FIGS. 4A-4F show example content of communication messages (e.g., SMS messages) having natural language (e.g., a language as a user may naturally use when writing a message to entity). For example, referring to FIG. 4A, the client device 402 detects a user interaction inputting content of an SMS message (e.g., the inquiry message described above in regard to act 202 of FIG. 2A) into the input area 430 of the communication thread GUI 418 of the messaging application GUI 412a, and the client device 402 adds the content of the inquiry message within a text bubble 420 to the communication thread GUI 418 (e.g., to the common window 428 of the communication thread GUI 418, to a chat session, etc.) of the messaging application GUI 412a. Moreover, the content of the inquiry message and text bubble 420 may include any of the elements of the inquiry message described above in regard to act 202 of FIG. 2A.

In addition to adding the content of the inquiry message as the text bubble 420 to the communication thread GUI 418 of the messaging application GUI 412a, the client device 402 may provide (e.g., send) the content of the inquiry message to the provider determination system 104. For example, the client device 402 may provide the content of the inquiry message to the provider determination system 104 in any of the manners described above in regard to act 202 of FIG. 2A. In some embodiments, the client device 402 may provide the content of the inquiry message to a chat application (e.g., a chat bot) of the provider determination system 104.

Referring to FIG. 4B, as described above in regard in regard to acts 214 through 220 of FIGS. 2A-2B, in response to receiving the content of the inquiry message within the text bubble 420, the provider determination system 104 may generate a location request and may provide the location request to the client device 402 according to any of the manners described above in regard to acts 222 and 224 of FIG. 2B.

In response to receiving the location request from the provider determination system 104, the client device 402 adds the location request within a chat bubble 422 to the communication thread GUI 418 of the messaging application GUI 412*a* for display to a user. As shown, the location request within the chat bubble 422 may include natural language asking the user where, geographically, the user needs/desires a provider.

Referring to FIG. 4C, upon adding the location request within the chat bubble 422 to the communication thread GUI 418 of the messaging application GUI 412*a*, the client device 402 may detect one or more user interactions inputting content of a location response message in response to the location request. For instance, the client device 402 and/or application 112 may detect one or more user interactions inputting a location according to any of the manners described above in regard to act 228 of FIG. 2B. Additionally, the client device 402 adds the content of the location response message within a text bubble 424 to the communication thread GUI 418 of the messaging application GUI 412*a*. Moreover, the client device 402 and/or application 112 may provide the content of the location response message to the provider determination system 104 via any of the manners described above in regard to act 230 of FIG. 2B.

Figure 4F:
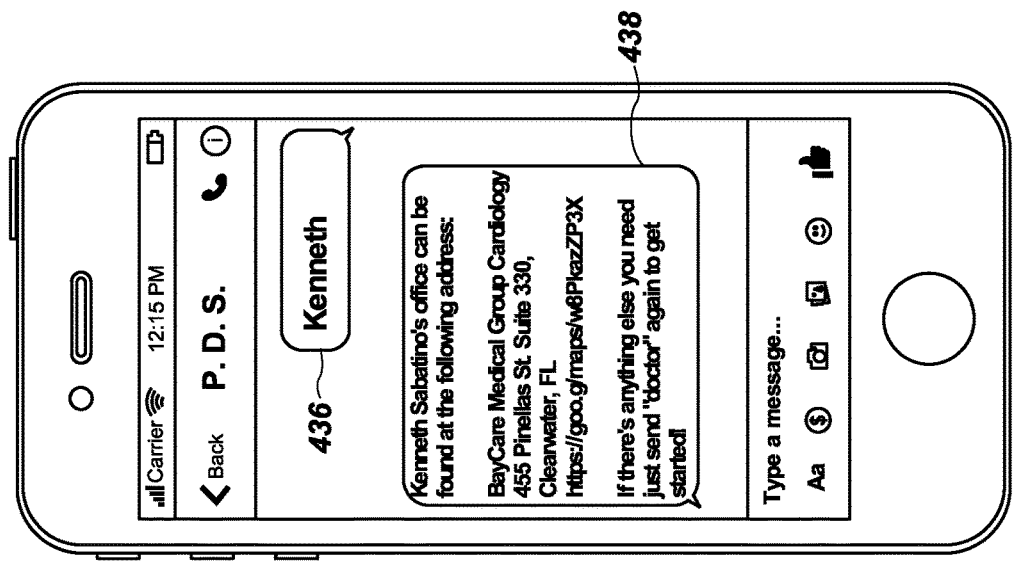
Figure 4E:
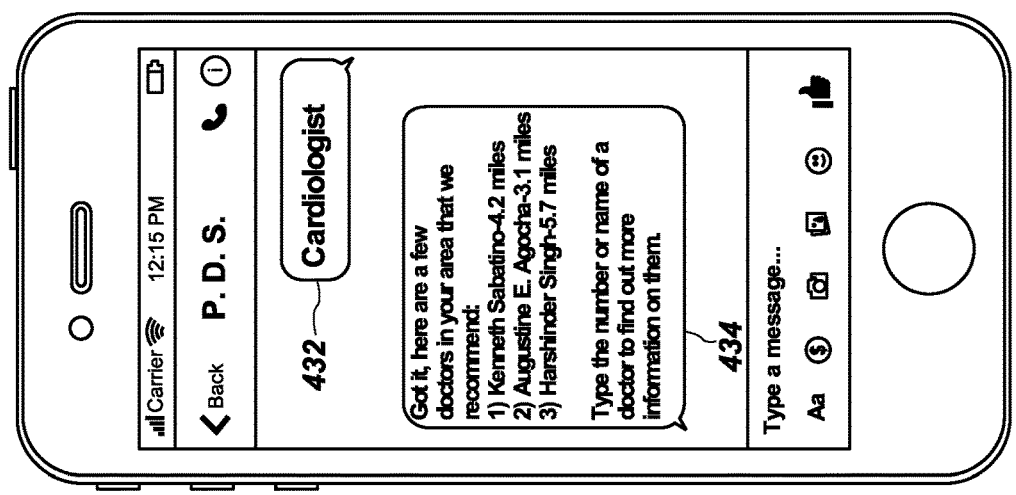
Figure 4D:
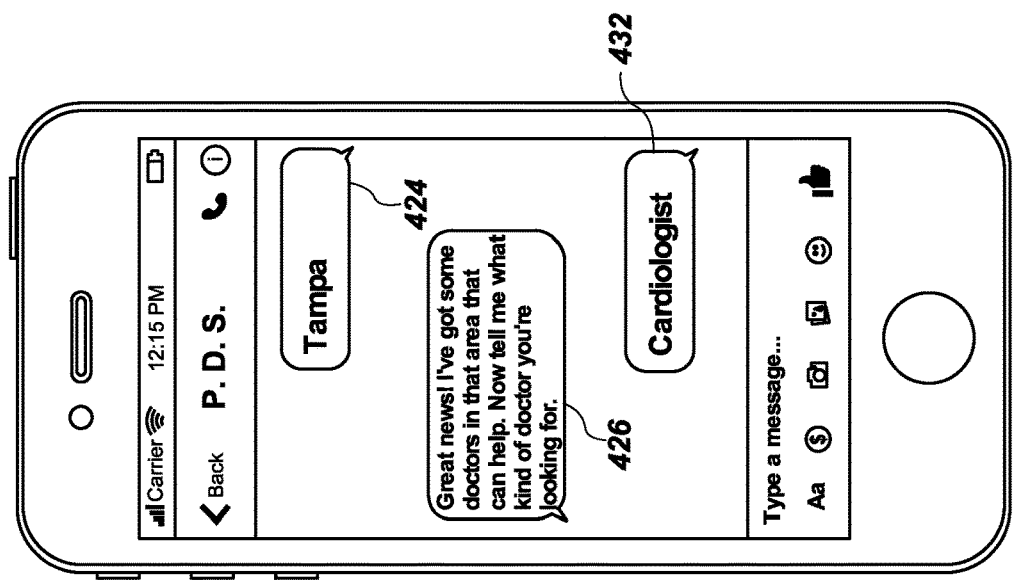

Referring to FIG. 4D, in response to receiving the content of the location response message, the provider determination system 104 may generate a provider type request according to any of the manners described above in regard to acts 236-242 of FIG. 2C. Furthermore, the provider determination system 104 may provide the provider type request to the client device 402 according to any of the manners described above in regard to acts 246 and 248 of FIG. 2C.

In response to receiving the request provider type request within a chat bubble 426 from the provider determination system 104, the client device 402 adds the content of the provider type request within the chat bubble 426 to the communication thread GUI 418 of the messaging application GUI 412*a* for display to a user. As shown, the provider type request within the chat bubble 426 may include natural language informing the user that the provider determination system 104 has record of providers near or at the location of the location response message and requesting a provider type designation.

Referring to FIG. 4D, upon adding the request for provider type request within the chat bubble 426 to the communication thread GUI 418 of the messaging application GUI 412*a*, the client device 402 may detect one or more user interactions inputting content of a provider type response message in response to the provider type request. For instance, the client device 402 and/or application 112 may detect one or more user interactions inputting a provider type according to any of the manners described above in regard to act 252 of FIG. 2D. Additionally, the client device 402 adds the content of the provider type response message within a text bubble 432 to the communication thread GUI 418 of the messaging application GUI 412*a*. Moreover, the client device 402 and/or application 112 may provide the content provider type response message to the provider determination system 104 via any of the manners described above in regard to act 254 of FIG. 2D.

Referring to FIG. 4E, in response to receiving the content of the provider type response message, the provider determination system 104 may generate a provider list message according to any of the manners described above in regard to acts 260-264 of FIGS. 2D and 2E. Furthermore, the provider determination system 104 may provide the provider list message to the client device 402 according to any of the manners described above in regard to acts 268 and 270 of FIG. 2E.

In response to receiving the provider list message from the provider determination system 104, the client device 402 adds the content of the provider list message within a chat bubble 434 to the communication thread GUI 418 of the messaging application GUI 412*a* for display to a user. As shown, the content of the provider list message within the chat bubble 434 may include natural language informing the user of one or more providers that match the provider type and location data provided by the user.

Referring to FIG. 4F, upon adding the request for provider list message within the chat bubble 434 to the communication thread GUI 418 of the messaging application GUI 412*a*, the client device 402 may detect one or more user interactions inputting content of a provider selection response message in response to the provider list message within the chat bubble 434. For instance, the client device 402 and/or application 112 may detect one or more user interactions inputting a provider's name or a number correlating to a provider within the provider list according to any of the manners described above in regard to act 274 of FIG. 2E. Additionally, the client device 402 adds the content of the provider selection response message within a text bubble 436 to the communication thread GUI 418 of the messaging application GUI 412*a*. Moreover, the client device 402 and/or application 112 may provide the content of the provider selection response message to the provider determination system 104 via any of the manners described above in regard to act 276 of FIG. 2E.

Referring to FIG. 4F, in response to receiving the content of the provider selection response message, the provider determination system 104 may generate a provider information message according to any of the manners described above in regard to acts 282 and 284 of FIG. 2F. Furthermore, the provider determination system 104 may provide the provider information message to the client device 402 according to any of the manners described above in regard to acts 288 and 290 of FIG. 2F.

In response to receiving the provider information message from the provider determination system 104, the client device 402 adds the content of the provider information message within a chat bubble 438 to the communication thread GUI 418 of the messaging application GUI 412*a* for display to a user. As shown, the provider information message within chat bubble 438 may include natural language informing the user of an address, phone number, and/or website of the selected provider. Furthermore, as is described below in regard to FIG. 7, in some embodiments, the provider information message within chat bubble 438 may include options to initiate further actions such as initiate a phone call with the selected provider, initiate a chat with the selected provider, schedule an appointment with the selected provider, etc.

Figure 5:
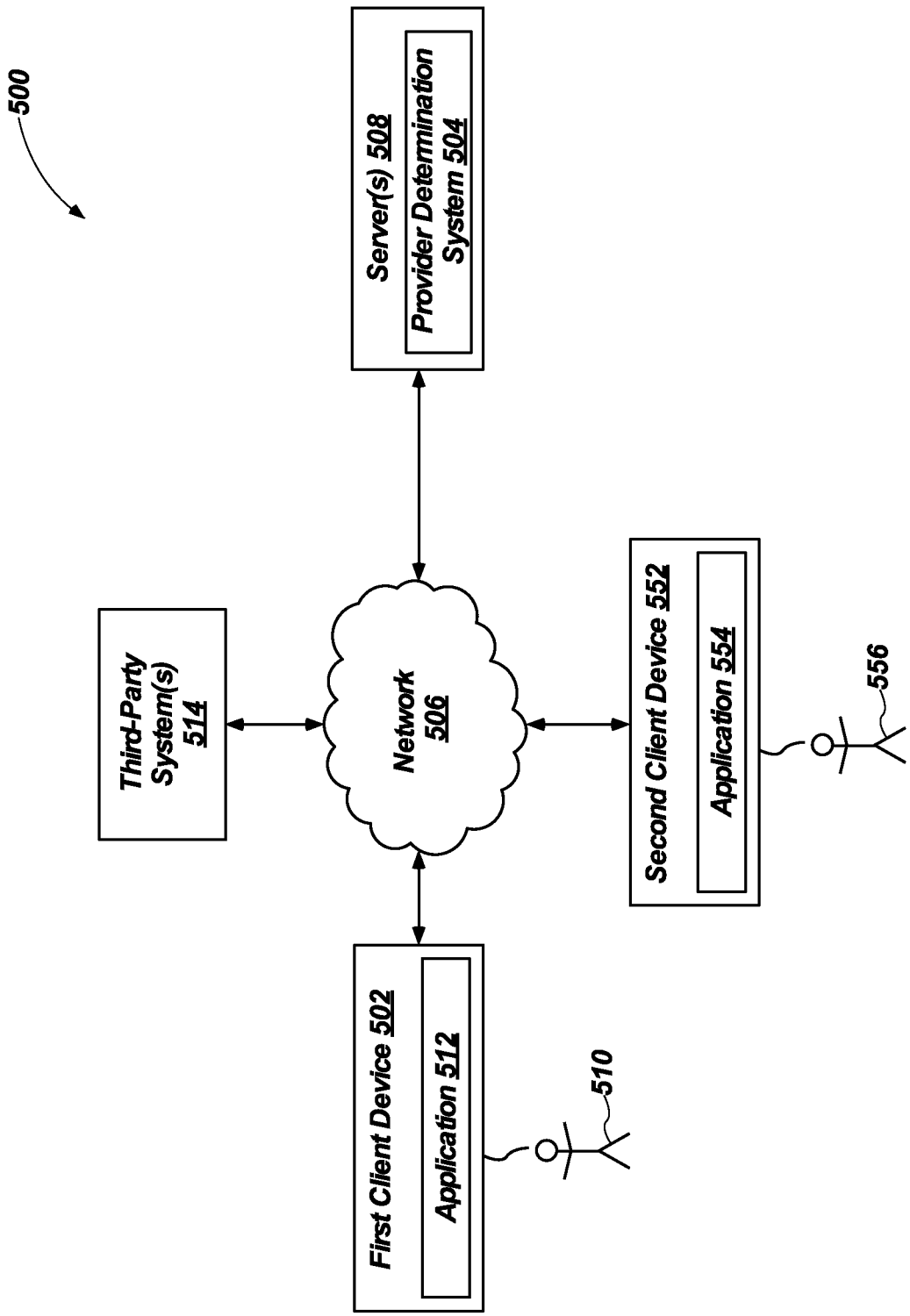
FIG. 5 illustrates another schematic representation of another environment within which a provider determination system can operate in accordance with one or more embodiments of the present disclosure.

FIG. 5 illustrates a schematic diagram of an environment 500 in which a provider determination system 504 may operate according to one or more embodiments of the present disclosure. Similar to the environment 100 of FIG. 1, the environment 500 includes a first client device 502, at least one server 508 including the provider determination system 504, a network 506, and one or more third-party system(s) 514. Furthermore, the first client device 502, at least one server 508 including the provider determination system 504, a network 506, and one or more third-party system(s) 514 may include any of the client devices, However, the environment 500 may include a second client device 552. Each the first and second client devices 502, 552 may include a respective application 512, 554 for facilitating communication (e.g., reading, composing, and/or sending messages (e.g., SMS messages)) between users 510, 556 and third parties and/or the provider determination system 104. The applications 512, 554 may include any of the applications described above in regard to FIGS. 1-2F and may operate via any of the manners described above in regard to FIGS. 1-2F. As is described in greater detail below in regard to FIGS. 6A-6C, is some embodiments, a first user 510 may utilize the first client device 502 to send a referral request message to the provider determination system 504 requesting that the provider determination system 504 refer one or more providers (e.g., provide information related to one or more providers) to a second user 556 of a second client device 552.

Figure 6A:
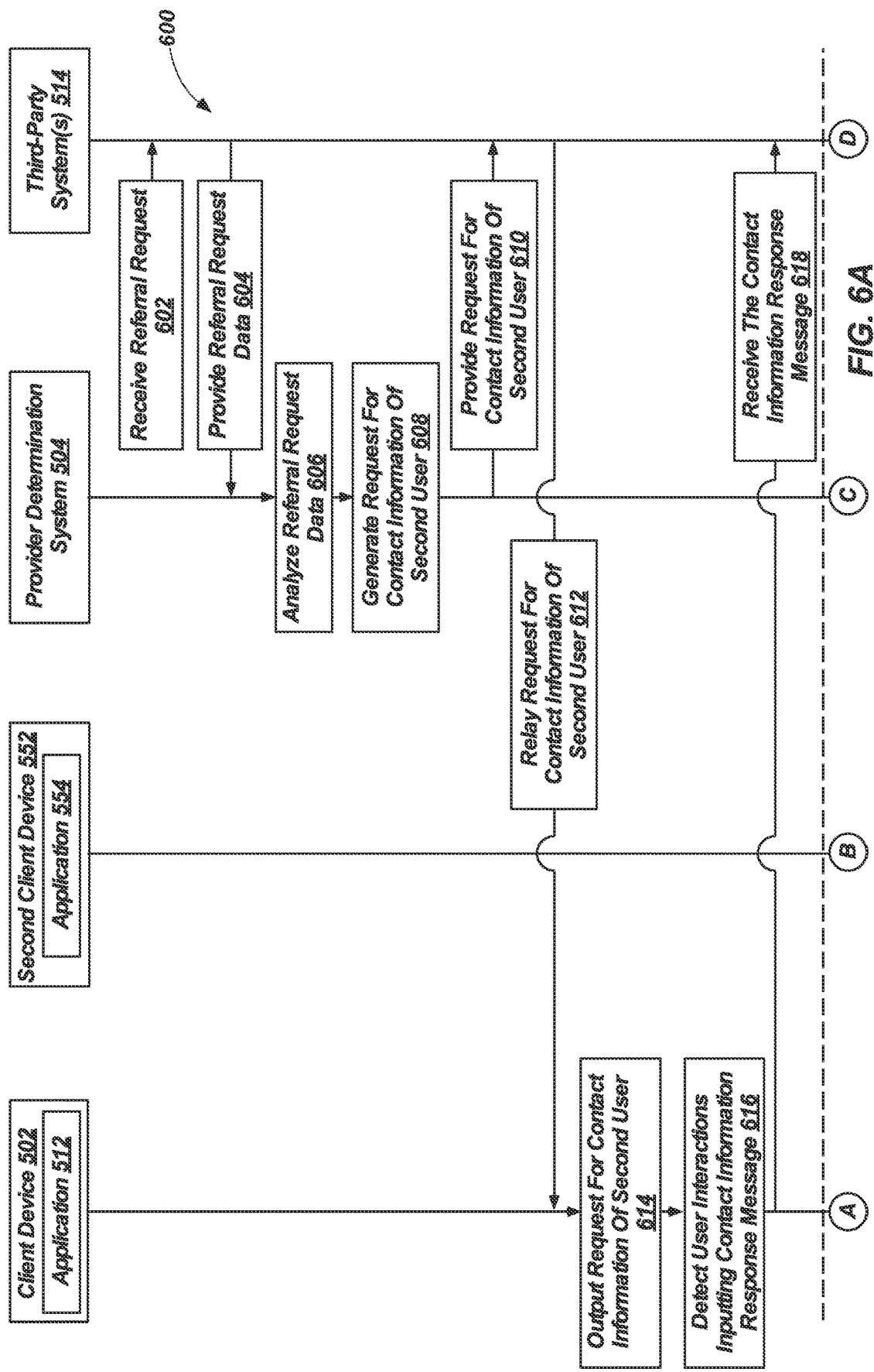
FIGS. 6A-6C illustrate a sequence flow diagram that a provider determination system can utilize to identify providers within a provider network and communicate with multiple client devices in accordance with one or more embodiments.
Figure 6B:
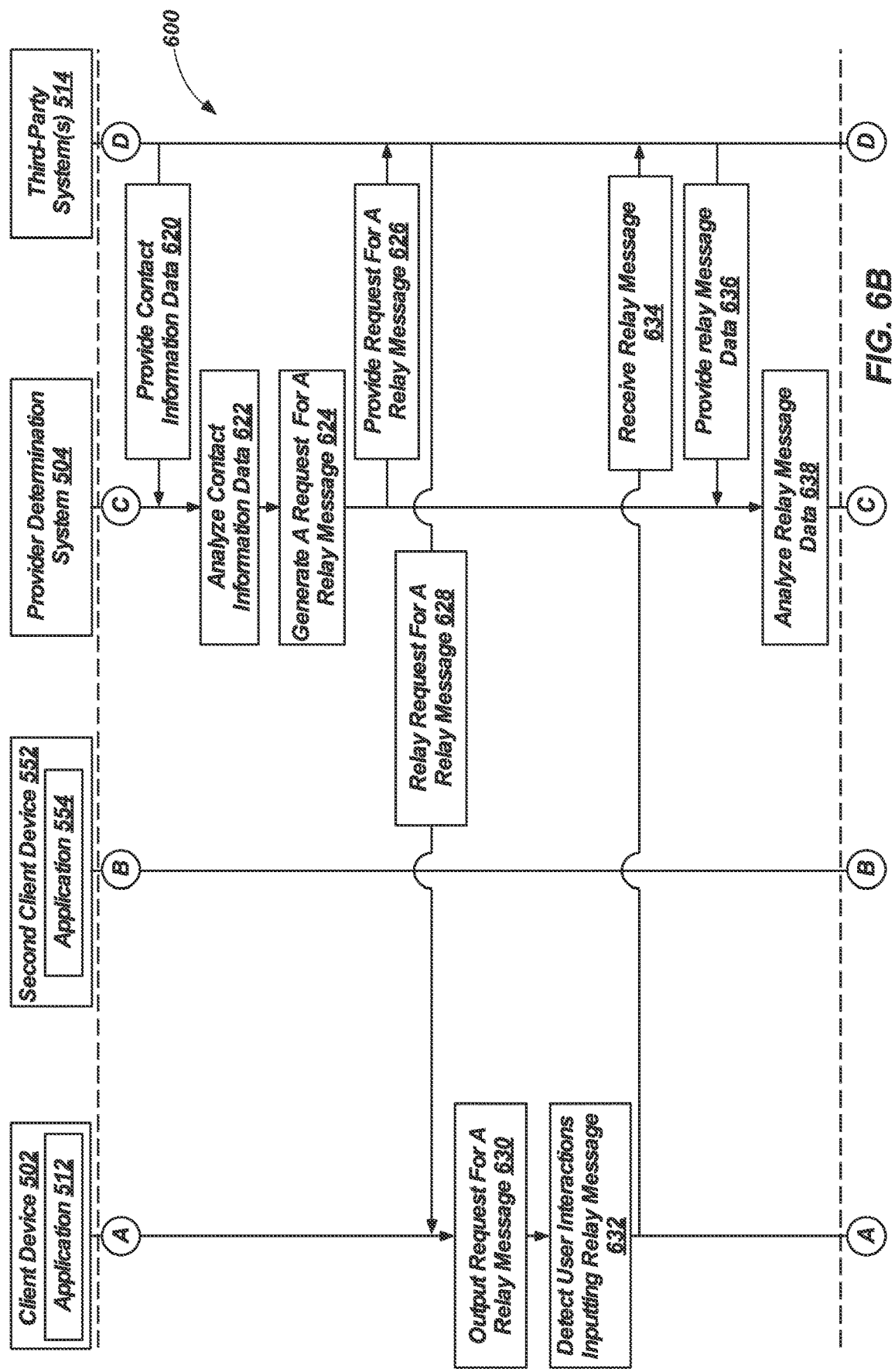
Figure 6C:
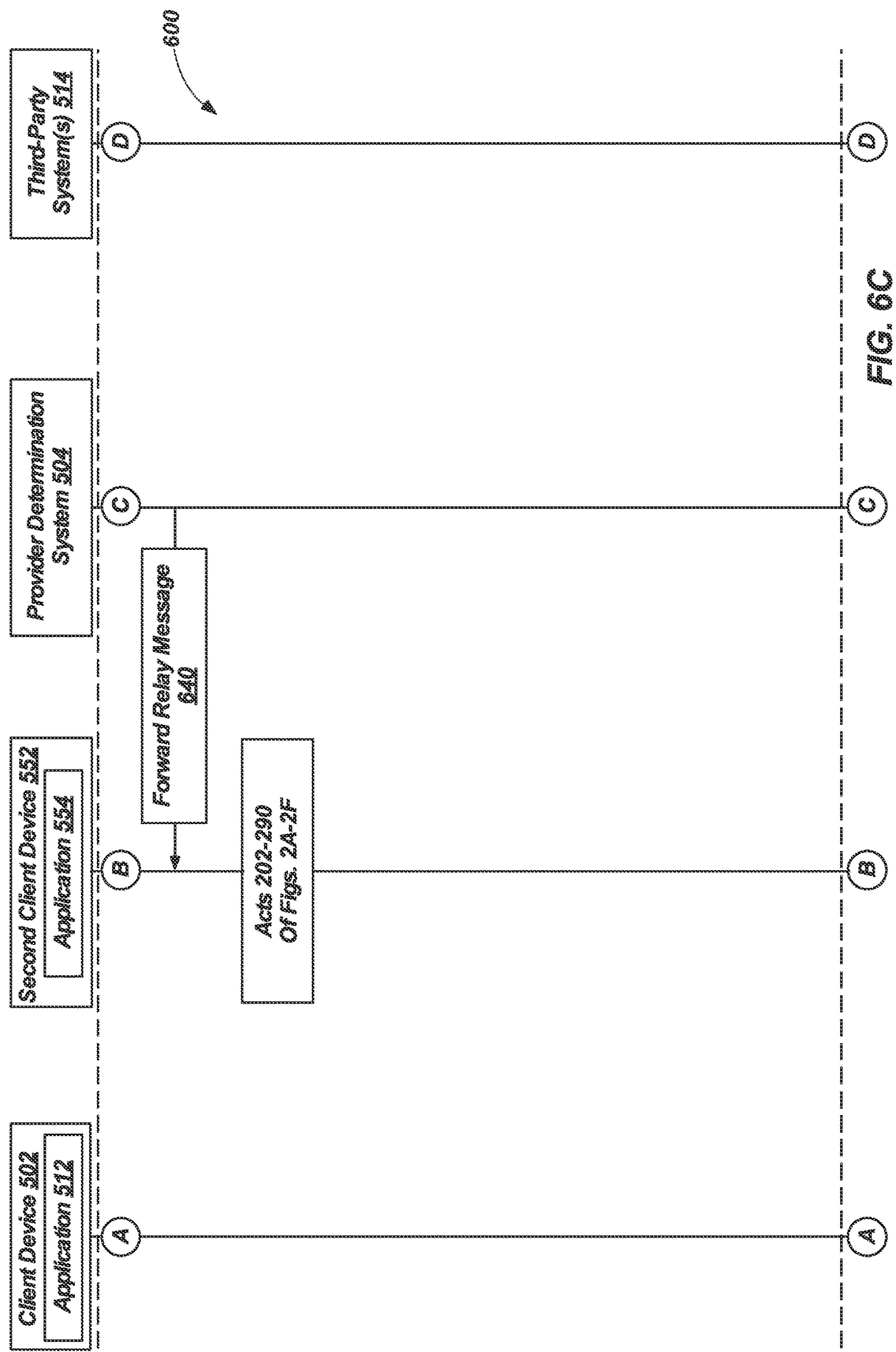

FIGS. 6A-6C illustrate a sequence-flow diagram 600 showing various steps of client devices 502, 552 and the provider determination system 504, in accordance with various embodiments of facilitating communications between client devices and the provider determination system 504. The client devices 502, 552, the third-party systems 514, and the provider determination system 504 shown in FIGS. 6A-6C may be example embodiments of the client devices 502, 552, the third-party systems 514, and the provider determination system 504 described in regard to FIG. 5.

As shown in act 602 of FIG. 6A, in some embodiments, the one or more third-party systems 514 receives a referral request message from the first client device 502. The referral request message may include any type of message described above in regard to FIGS. 1-2F. In some embodiments the referral request message may include a request for the provider determination system 504 to refer one or more providers (e.g., provide information related to one or more providers) to a second user 556 of a second client device 552. For instance, the referral request message may include a message such as "refer a doctor." The one or more third-party systems 514 may receive the referral request message via any of the manners described above in regard to FIGS. 2A-2F. Furthermore, although not shown in FIG. 6A, the one or more third-party systems 514 may analyze the referral request message via any of the manners described above in regard to FIGS. 2A-2F to determine a meaning of and categorize the message.

Furthermore, upon analyzing the referral request message, the one or more third-party systems 514 may provide the message, any matched category (e.g., endpoint) data, and/or the determined and derived meanings of the referral request message (referred to herein collectively as "referral request data") to the provider determination system 504, as shown in act 604 of FIG. 6A. The one or more third-party systems 514 may provide the referral request data to the provider determination system 504 via any of the networks and communication methods described herein.

Upon receiving the referral request data from the one or more third-party systems 514, the provider determination system 504 may further analyze the referral request data, as shown in act 606 of FIG. 6A. For instance, the provider determination system 504 may analyze the referral request data via any of the manners, methods, and systems described above in regard to acts 214-218 of FIG. 2A.

In response to analyzing the message, the provider determination system 504 generates a request for contact information (e.g., a phone number, tag, handle, email address) of the second user 556 and/or second client device 552, as shown in act 608 of FIG. 6A. The provider determination system 504 may generate the request for contact information to match a determined type of received referral request message. For instance, in some embodiments, the request for contact information may include an SMS message. In other embodiments, the request for contact information may include any of the other types of messages described above. The provider determination system 504 may generate the request for contact information according to any of the manners described above in regard to act 220 of FIG. 2B.

Upon generating the request for contact information, the provider determination system 504 may provide the request for contact information to the one or more third-party systems 514 (e.g., the messaging API) for relay to the client device 502, as shown in act 610 of FIG. 6A. The provider determination system 504 may provide the request for contact information to the one or more third-party systems 514 via any of the networks and communication methods described herein.

Upon receiving the request for contact information from the provider determination system 504, the one or more third-party systems 514 (e.g., the messaging API) may relay the request for contact information to the client device 502, as shown in act 612 of FIG. 6A. The one or more third-party systems 514 (e.g., the messaging API) may provide the location request to the client device 502 via any of the networks and communication methods described herein.

In response to receiving the request for contact information, the application 112 and/or client device 102 outputs the request for contact information, as shown in act 614 of FIG. 6A. For instance, the application 512 and/or client device 502 may output the request for contact information via any of the methods described above in regard to act 226 of FIG. 2B. For example, the application 512 and/or client device 502 may output the request for contact information as a text message, notification, email, audio message, video message, etc.

In response to outputting the request for contact information, the application 512 and/or client device 502 detects a user interaction inputting a contact information response message, as shown in act 616 of FIG. 6A. Furthermore, the types of user interactions may include any of the user interactions described above in regard to act 228 of FIG. 2B. The contact information response message may include a phone number, a handle, an email address, a unique identifier, etc., of the second user 556 and/or the second client device 552.

In response to the client device 502 detecting a user interaction inputting a contact information response message, the one or more third-party systems 514 receives the contact information response message, as shown in act 618 of FIG. 6A. For example, the one or more third-party systems 514 may receive the contact information response message from the client device 502 and/or application 512 of the first client device 502 via a network (e.g., a cellular network). In other words, upon detecting a user interaction inputting the contact information response message, the first client device 502 and/or application 512 of the first client device 502 may provide the contact information response message to the one or more third-party systems 514. Furthermore, the one or more third-party systems 514 may receive the contact information response message via any of the manners described above in regard to act 202 of FIG. 2A. Moreover, although not shown in FIG. 6A, the one or more third-party systems 514 may analyze the contact information response message via any of the manners described above in regard to FIGS. 2A-2F to determine a meaning and categorize the contact information response message.

Furthermore, upon analyzing the contact information response message, the one or more third-party systems 514 may provide the contact information response message, any matched category (e.g., endpoint) data, and/or the determined and derived meanings of the contact information response message (referred to herein collectively as "contact information data") to the provider determination system 504, as shown in act 620 of FIG. 6B. The one or more third-party systems 514 may provide the contact information data to the provider determination system 504 via any of the networks and communication methods described herein.

Upon receiving the contact information data from the one or more third-party systems 514, the provider determination system 504 may further analyze the contact information data, as shown in act 622 of FIG. 6B. For instance, the provider determination system 504 may contact information response message via any of the manners, methods, and systems described above in regard to acts 214-218 of FIG. 2A.

In response to analyzing the contact information response message, the provider determination system 504 generates a request for a relay message to be relayed the second user 556 and/or second client device 552, as shown in act 624 of FIG. 6B. The provider determination system 504 may generate the request for a relay message to match a determined type of received message. For instance, in some embodiments, the request for a relay message may include an SMS message. In other embodiments, the request for a relay message may include any of the other types of messages described above. The provider determination system 504 may generate the request for a relay message according to any of the manners described above in regard to act 220 of FIG. 2B.

Upon generating the request for a relay message, the provider determination system 504 may provide the request for a relay message to the one or more third-party systems 514 (e.g., the messaging API) for relay to the client device 502, as shown in act 626 of FIG. 6B. The provider determination system 504 may provide request for a relay message to the one or more third-party systems 514 via any of the networks and communication methods described herein.

Upon receiving the request for a relay message from the provider determination system 504, the one or more third-party systems 514 (e.g., the messaging API) may relay the request for a relay message to the client device 502, as shown in act 628 of FIG. 6B. The one or more third-party systems 514 (e.g., the messaging API) may provide the request for a relay message to the client device 502 via any of the networks and communication methods described herein.

In response to receiving the request for a relay message, the application 112 and/or client device 102 outputs the request for a relay message, as shown in act 630 of FIG. 6B. For instance, the application 512 and/or client device 502 may output the request for a relay message via any of the methods described above in regard to act 226 of FIG. 2B. For example, the application 512 and/or client device 502 may output the request for a relay message as a text message, notification, email, audio message, video message, etc.

In response to outputting the request for a relay message, the application 512 and/or client device 502 detects a user interaction inputting a relay message, as shown in act 632 of FIG. 6B. Furthermore, the types of user interactions may include any of the user interactions described above in regard to act 228 of FIG. 2B. As a non-limiting example, the relay message may be "Hello Luke, this is your father, Darth Vader. This service may help you find the doctor that you need to replace your missing hand. Just text the word 'doctor' to this number."

In response to the client device 502 detecting a user interaction inputting a relay message, the one or more third-party systems 514 receives the relay message, as shown in act 634 of FIG. 6B. For example, the one or more third-party systems 514 may receive the relay message from the client device 502 and/or application 512 of the first client device 502 via a network (e.g., a cellular network). In other words, upon detecting a user interaction inputting the relay message, the first client device 502 and/or application 512 of the first client device 502 may provide the relay message to the one or more third-party systems 514. Furthermore, the one or more third-party systems 514 may receive the relay message via any of the manners described above in regard to act 202 of FIG. 2A. Moreover, although not shown in FIG. 6A, the one or more third-party systems 514 may analyze the relay message via any of the manners described above in regard to FIGS. 2A-2F to determine a meaning and categorize the relay message.

Furthermore, upon analyzing the relay message, the one or more third-party systems 514 may provide the relay message, any matched category (e.g., endpoint) data, and/or the determined and derived meanings of the relay message to the provider determination system 504 (referred to hereinafter collectively as "relay message data"), as shown in act 636 of FIG. 6B. The one or more third-party systems 514 may provide the relay message, the matched category (e.g., endpoint) data, and/or the determined and derived meanings of the relay message to the provider determination system 504 via any of the networks and communication methods described herein.

Upon receiving the relay message data, the provider determination system 504 may further analyze the relay message data, as shown in act 638 of FIG. 6B. For instance, the provider determination system 504 may analyze the relay message via any of the manners, methods, and systems described above in regard to acts 214-218 of FIG. 2A.

In response to analyzing the relay message, the provider determination system 504 forwards the relay message to the second client device 552, as shown in act 640 of FIG. 6C. Furthermore, in response to receiving an inquiry message from the second client device 552 including a request related to services provided by the provider determination system 504, the provider determination system 504 may initiate the process (e.g., acts 202-290) described above in regard to FIGS. 2A-2F in whole or in part.

Figure 7:
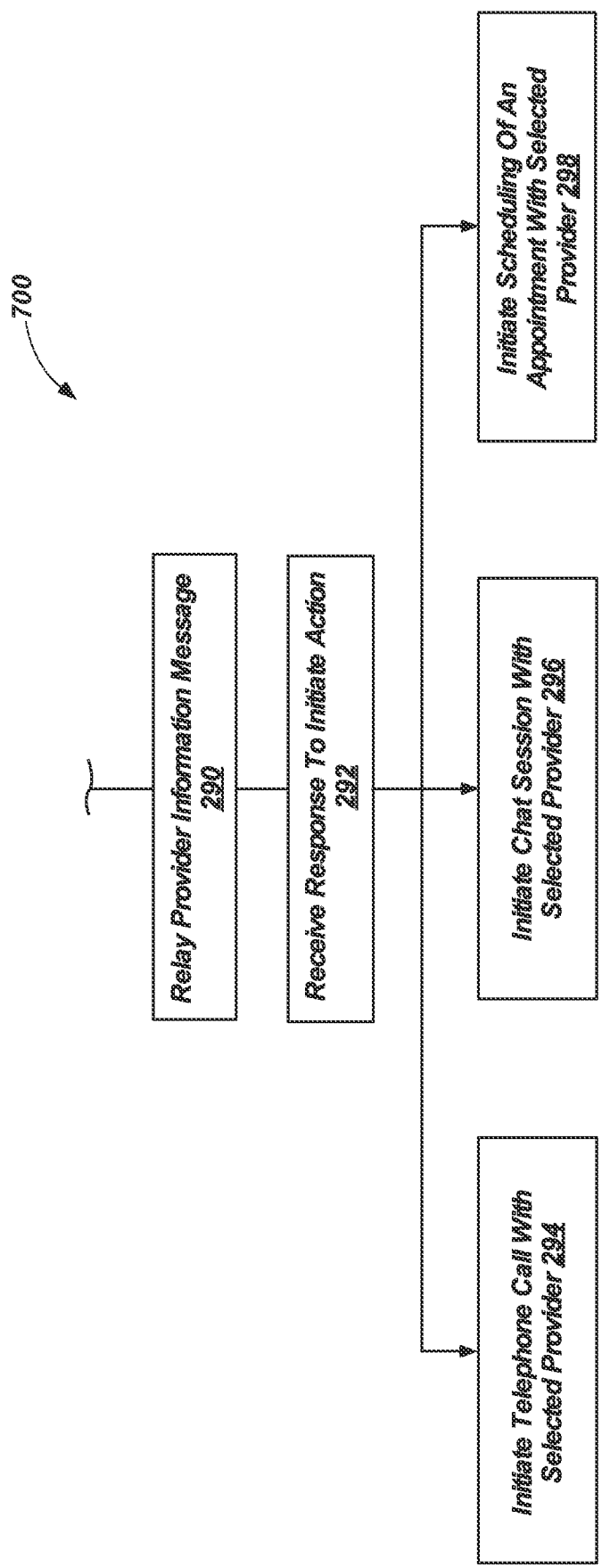
FIG. 7 illustrates a sequence flow diagram that a provider determination system can utilize to initiate actions in regard to a selected provider in accordance with one or more embodiments of the present disclosure.

FIG. 7 illustrates a sequence-flow diagram 700 showing various steps of the provider determination system 104, in accordance with various embodiments of facilitating communications between client devices and the provider determination system 104. In particular, FIG. 7 shows acts that may occur after act 290 of FIGS. 2F and 6C. For example, when the provider information message generated by the provider determination system 104 include options to initiate further actions in regard the selected provider, the provider determination system 104 may operate according to the actions depicted in FIG. 7. As shown in act 292 of FIG. 7, in response to providing the provider information message with options to initiate further actions in regard the selected provider, the provider determination system 104 received a response from the client device 102 to initiate an action in regard to the selected provider, as shown in act 292 of FIG. 7. In some embodiments, initiating an action in regard to the selected provider includes initiating a telephone call with the selected provider, as shown in act 294 of FIG. 7. In additional embodiments, initiating an action in regard to the selected provider includes initiating a chat session with the selected provider, as shown in act 296 of FIG. 7. In further embodiments, initiating an action in regard to the selected provider includes initiating scheduling of an appointment with the selected provider as shown in act 298 of FIG. 7.

For instance, in response to receiving a response from the client device 102 to initiate an action in regard to the selected provider, the provider determination system 104 may interface with one or more APIs associated with the selected provider, communication providers, and/or websites to initiate the action.

Referring to FIGS. 1-7 together, in some embodiments, instead of identifying providers or in addition to identifying providers based on location data, the provider determination system 104 may identify (e.g., filter providers) based on current wait times, distance (e.g., radius) from public transportation, or any other criteria.

Furthermore, in one or more embodiments, the provider determination system 104 may provide a referral service. For example, a user may send a message to the provider determination system 104 via any of the manners described above, and the message may include the key word "referral." In response, the provider determination system 104 may provide a response message to the user asking to whom the user was referred. Upon receiving information related to who the user was referred, the provider determination system 104 may provide a message to the user indicating whether the referred provider is a recommended provider (e.g., covered within the user's insurance), and if the referred provider is not a recommender provider, the provider determination system 104 may provide a list of recommended provider matching the referred provider's specialty.

Additionally, in one or more embodiments, the provider determination system 104 may provide a recommendation service for a first user to recommend a provider to a second user (e.g., for a father to recommend a provider for a daughter who is away at college). For example, the first user may send a message to the provider determination system 104 via any of the manners described above, and the message may include the key word "recommend." In response, the provider determination system 104 may provide a response message to the first user asking for contact information of the second user (e.g., of the person to which the first user wants to send a recommendation). Upon receiving contact information for the second user, the provider determination system 104 may send a message to the second user to initiate any of the processes described above in regard to FIGS. 1-7.

Moreover, in one or more embodiments, the provider determination system 104 may provide a scheduling service for a user to immediately schedule an appointment with a provider. For example, the user may send a message to the provider determination system 104 via any of the manners described above, and the message may include the key word "schedule." In response, the provider determination system 104 may provide a response message including a request for location. For example, the provider determination system 104 may imitate acts 220-266 of FIGS. 2B-2E. However, the provider determination system 104 may prioritize (e.g., order) the provider list based on current wait times.

Figure 8:
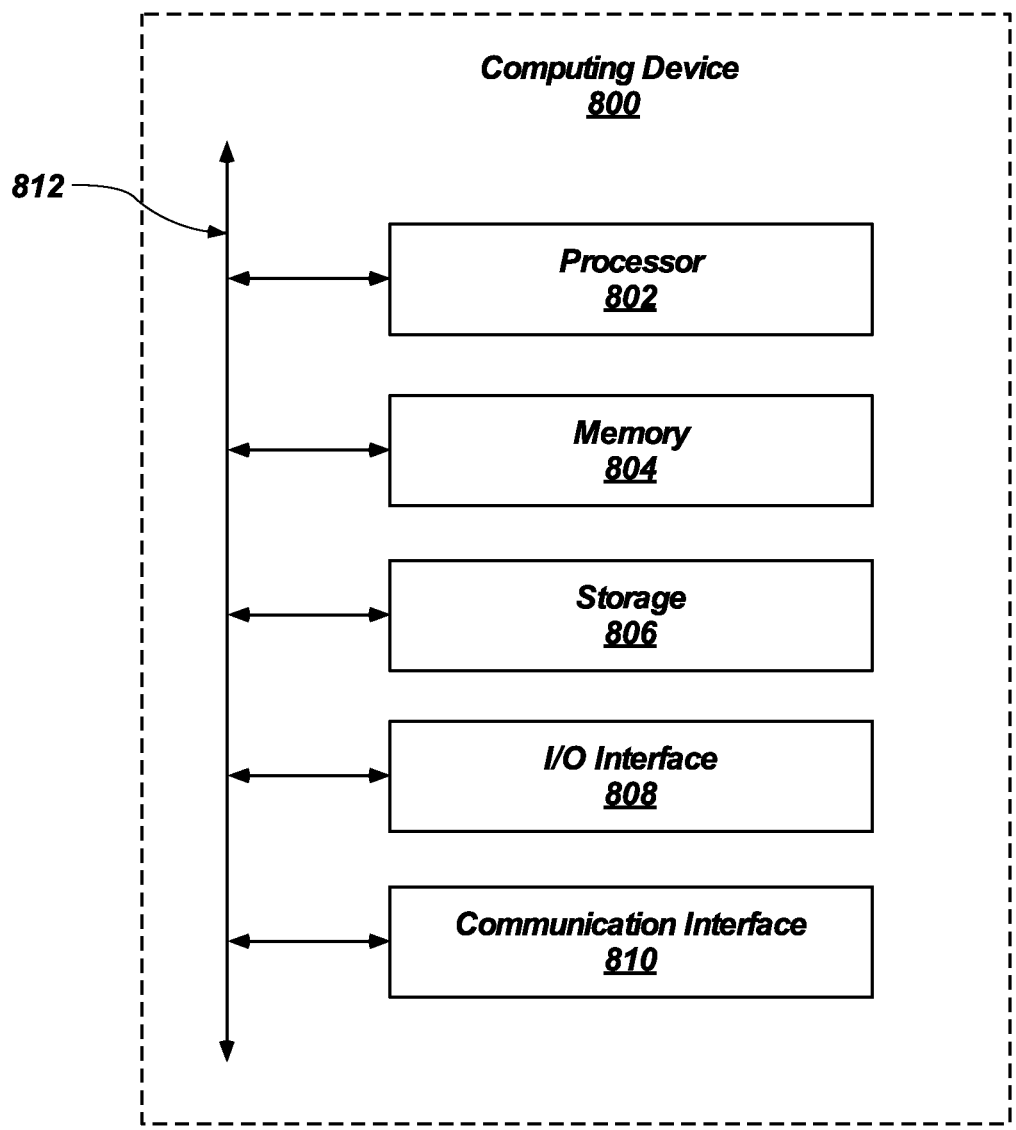
FIG. 8 illustrates a block diagram of an exemplary computing device in accordance with one or more embodiments.

FIG. 8 is a block diagram of an exemplary computing device 800 that may be utilized as a client device (e.g., client device 102) and/or a provider determination system (e.g., provider determination system 104) that may be configured to perform one or more of the processes described above. One will appreciate that one or more computing devices may implement the computing device 800. The computing device 800 can comprise a processor 802, a memory 804, a storage device 806, an I/O interface 808, and a communication interface 810, which may be communicatively coupled by way of a communication infrastructure 812. While an exemplary computing device is shown in FIG. 8, the components illustrated in FIG. 8 are not intended to be limiting. Additional or alternative components may be used in other embodiments. Furthermore, in certain embodiments, the computing device 800 can include fewer components than those shown in FIG. 8. Components of the computing device 800 shown in FIG. 8 will now be described in additional detail.

In one or more embodiments, the processor 802 includes hardware for executing instructions, such as those making up a computer program. As an example and not by way of limitation, to execute instructions, the processor 802 may retrieve (or fetch) the instructions from an internal register, an internal cache, the memory 804, or the storage device 806 and decode and execute them. In one or more embodiments, the processor 802 may include one or more internal caches for data, instructions, or addresses. As an example and not by way of limitation, the processor 802 may include one or more instruction caches, one or more data caches, and one or more translation lookaside buffers (TLBs). Instructions in the instruction caches may be copies of instructions in the memory 804 or the storage 806.

The memory 804 may be used for storing data, metadata, and programs for execution by the processor(s). The memory 804 may include one or more of volatile and non-volatile memories, such as Random Access Memory ("RAM"), Read-Only Memory ("ROM"), a solid state disk ("SSD"), Flash memory, Phase Change Memory ("PCM"), or other types of data storage. The memory 804 may be internal or distributed memory.

The storage device 806 includes storage for storing data or instructions. As an example and not by way of limitation, storage device 806 can comprise a non-transitory storage medium described above. The storage device 806 may include a hard disk drive (HDD), a floppy disk drive, flash memory, an optical disc, a magneto-optical disc, magnetic tape, or a Universal Serial Bus (USB) drive or a combination of two or more of these. The storage device 806 may include removable or non-removable (or fixed) media, where appropriate. The storage device 806 may be internal or external to the computing device 800. In one or more embodiments, the storage device 806 is non-volatile, solid-state memory. In other embodiments, the storage device 806 includes read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these.

The I/O interface 808 allows a user to provide input to, receive output from, and otherwise transfer data to and receive data from computing device 800. The I/O interface 808 may include a mouse, a keypad or a keyboard, a touch screen, a camera, an optical scanner, network interface, modem, other known I/O devices or a combination of such I/O interfaces. The I/O interface 808 may include one or more devices for presenting output to a user, including, but not limited to, a graphics engine, a display (e.g., a display screen), one or more output drivers (e.g., display drivers), one or more audio speakers, and one or more audio drivers.

In certain embodiments, the I/O interface 808 is configured to provide graphical data to a display for presentation to a user. The graphical data may be representative of one or more graphical user interfaces and/or any other graphical content as may serve a particular implementation.

The communication interface 810 can include hardware, software, or both. In any event, the communication interface 810 can provide one or more interfaces for communication (such as, for example, packet-based communication) between the computing device 800 and one or more other computing devices or networks. As an example and not by way of limitation, the communication interface 810 may include a network interface controller (NIC) or network adapter for communicating with an Ethernet or other wire-based network or a wireless NIC (WNIC) or wireless adapter for communicating with a wireless network, such as a WI-FI.

Additionally or alternatively, the communication interface 810 may facilitate communications with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the communication interface 810 may facilitate communications with a wireless PAN (WPAN) (such as, for example, a BLUETOOTH® WPAN™), a WI-FI network, a WI-MAX network, a cellular telephone network (such as, for example, a Global System for Mobile Communications (GSM) network), or other suitable wireless network or a combination thereof.

Additionally, the communication interface 810 may facilitate communications various communication protocols. Examples of communication protocols that may be used include, but are not limited to, data transmission media, communications devices, Transmission Control Protocol ("TCP"), Internet Protocol ("IP"), File Transfer Protocol ("FTP"), Telnet, Hypertext Transfer Protocol ("HTTP"), Hypertext Transfer Protocol Secure ("HTTPS"), Session Initiation Protocol ("SIP"), Simple Object Access Protocol ("SOAP"), Extensible Mark-up Language ("XML") and variations thereof, Simple Mail Transfer Protocol ("SMTP"), Real-Time Transport Protocol ("RTP"), User Datagram Protocol ("UDP"), Global System for Mobile Communications ("GSM") technologies, Code Division Multiple Access ("CDMA") technologies, Time Division Multiple Access ("TDMA") technologies, Short Message Service ("SMS"), Multimedia Message Service ("MMS"), radio frequency ("RF") signaling technologies, Long Term Evolution ("LTE") technologies, wireless communication technologies, in-band and out-of-band signaling technologies, and other suitable communications networks and technologies.

The communication infrastructure 812 may include hardware, software, or both that couples components of the computing device 800 to each other. As an example and not by way of limitation, the communication infrastructure 812 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

The embodiments of the disclosure described above and illustrated in the accompanying drawing figures do not limit the scope of the invention, since these embodiments are merely examples of embodiments of the invention, which is defined by the appended claims and their legal equivalents. Any equivalent embodiments are intended to be within the scope of this invention. Indeed, various modifications of the present disclosure, in addition to those shown and described herein, such as alternative useful combinations of the content features described, may become apparent to those skilled in the art from the description. Such modifications and embodiments are also intended to fall within the scope of the appended claims and legal equivalents.

We claim:

1. A non-transitory computer-readable medium storing instructions thereon that, when executed by at least one processor, cause the at least one processor to perform steps comprising:
   receiving, from a client device, a request for information for a provider within a user's provider network;
   analyzing the request for information to determine a meaning of the request for information;
   in response to determining a meaning of the request for information, providing a request for location information and a provider type request to the client device;
   in response to receiving a location response and a provider type response, generating one or more queries based, at least in part, on query parameters including a specialty of a provider and a user location, the query parameters based, at least in part, on the provider type response and the location response;
   determining whether there are providers within the user's provider network that match both a location identified in the location response and a provider type identified in the provide type response via the one or more queries;
   in response to identifying one or more providers that match both the location identified in the location response and the provider type identified in the provide type response, generating a provider list and providing the provider list to the client device;
   in response to receiving a provider selection selecting a provider from the provider list, generating a provider information response including information related to the selected provider and an option to initiate an action in related to the selected provider;
   providing the provider information response to the client device;
   receiving an indication from the client device to initiate the action related to the selected provider; and
   initiating the action related to the selected provider.

2. The non-transitory computer-readable medium of claim 1, wherein initiating the action related to the selected provider comprises at least one of initiating a telephone call with the selected provider, initiating a communication session with the selected provider, scheduling an appointment with the selected provider, or forwarding the provider information to another client device.

3. The non-transitory computer-readable medium of claim 1, wherein providing a request for location information and a provider type request comprises generating the request for location information and the provider type request to match a communication type of the inquiry.

4. The non-transitory computer-readable medium of claim 1, wherein providing a request for location information and a provider type request comprises generating the request for location information and the provider type request via a natural language generation system.

5. The non-transitory computer-readable medium of claim 1, wherein receiving the request for information comprises receiving at least one of an SMS message, an audio message, a video message, an email message, or a messenger message.

6. The non-transitory computer-readable medium of claim 1, wherein receiving the request for information comprises receiving the request for information from a third-party system at a provider determination system.

7. The non-transitory computer-readable medium of claim 1, wherein the instructions when executed by the at least one processor, cause the at least one processor to perform steps comprising:
   in response to receiving the request for information, generating a request for location information; and
   sending request for location information to client device.

8. The non-transitory computer-readable medium of claim 7, wherein the instructions when executed by the at least one processor, cause the at least one processor to perform steps comprising:
   receiving, from the client device, a location response;
   identifying a location indicated in the location response as a query parameter; and
   determining whether a location identified by the location response is currently supported by a provider determination system.

9. The non-transitory computer-readable medium of claim 8, wherein the instructions when executed by the at least one processor, cause the at least one processor to perform steps comprising:
   in response to determining that the location is currently supported by the provider determination system, generating a provider type request; and
   sending the provider type request to the client device.

10. The non-transitory computer-readable medium of claim 9, wherein the instructions when executed by the at least one processor, cause the at least one processor to perform steps comprising:
    receiving, from the client device, a provider type response;
    identifying a provider type indicated in the provider type response as a query parameter; and
    determining, via one or more queries of a provider database, whether there are providers within the user's provider network that match both the location identified in the location response and a provider type identified in the provide type response.

11. The non-transitory computer-readable medium of claim 10, wherein the instructions when executed by the at least one processor, cause the at least one processor to perform steps comprising:
    in response to identifying one or more providers that match both the location identified in the location response and the provider type identified in the provide type response, generating a provider list;
    sending the provider list to the client device;
    receiving, from the client device, a provider selection response selecting a provider from the provider list;
    in response to receiving the provider selection response, generating a provider information response including information related to the selected provider; and
    sending the provider information response to the client device.

12. The non-transitory computer-readable medium of claim 10, wherein determining whether there are providers within a user's provider network that match the location identified in the location response comprises determining whether there are providers within a radius of one of five, ten, twenty-five, fifty, or one hundred miles from the location.

13. The non-transitory computer-readable medium of claim 1, wherein analyzing the request for information comprises analyzing the request for information via a natural language process comprising at least one machine learning technique.

14. The non-transitory computer-readable medium of claim 1, wherein the instructions when executed by the at least one processor, cause the at least one processor to perform steps comprising:
    identifying the user's provider network based on one of a unique identifier of a user or a provider determination system identifier to which the request for information is sent.

* * * * *